(12) United States Patent
Bayer et al.

(10) Patent No.: US 7,511,174 B2
(45) Date of Patent: *Mar. 31, 2009

(54) SOLID AND CRYSTALLINE IBANDRONIC ACID

(75) Inventors: Thomas Bayer, Tel Aviv (IL); Ben-Zion Dolitzky, Petach Tiqva (IL); Revital Lifshitz-Liron, Hertzlia (IL); Inna Perutski, Hadera (IL); Michael Pinchasov, Dover, NJ (US)

(73) Assignee: Teva Pharmaceutical Industries Ltd, Petah Tiqva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 11/525,804

(22) Filed: Sep. 22, 2006

(65) Prior Publication Data

US 2007/0161606 A1 Jul. 12, 2007

Related U.S. Application Data

(63) Continuation of application No. 11/331,995, filed on Jan. 12, 2006, now abandoned, which is a continuation of application No. 11/165,481, filed on Jun. 22, 2005, now abandoned.

(60) Provisional application No. 60/582,500, filed on Jun. 23, 2004, provisional application No. 60/620,016, filed on Oct. 18, 2004, provisional application No. 60/690,868, filed on Jun. 16, 2005.

(51) Int. Cl.
C07F 9/02 (2006.01)

(52) U.S. Cl. .............................. 564/15; 564/21; 564/22

(58) Field of Classification Search .................. 564/15, 564/21, 22; 546/22; 562/21
See application file for complete search history.

(56) References Cited

U.S. PATENT DOCUMENTS

| | | | | |
|---|---|---|---|---|
| 4,927,814 A | * | 5/1990 | Gall et al. | 514/108 |
| 6,419,955 B1 | * | 7/2002 | Gabel et al. | 424/466 |
| 7,038,083 B2 | * | 5/2006 | Lidor-Hadas et al. | 564/15 |
| 7,214,818 B2 | * | 5/2007 | Baetz et al. | 562/13 |
| 2007/0112197 A1 | * | 5/2007 | Grassi et al. | 546/22 |

FOREIGN PATENT DOCUMENTS

| | | |
|---|---|---|
| WO | WO 03/097655 A1 | 11/2003 |
| WO | WO 2005/044831 A2 | 5/2005 |
| WO | WO 2005/063779 A2 | 7/2005 |

OTHER PUBLICATIONS

Caira M. R., "Crystalline polymorphism of organic compounds," Topics in Current Chemistry (1998) vol. 198, pp. 163-208, XP001156954.
Craig D. Q. M. et al., "The relevance of the amorphous state to pharmaceutical dosage forms: glassy drugs and freeze dried systems," International Journal of Pharmaceutics (Mar. 15, 1999) vol. 179, No. 2, pp. 179-207, XP002274233.
Hancock, B. C. et al., "Characteristics and Significance of the Amorphous State in Pharmaceutical Systems," Journal of Pharmaceutical Sciences (Jan. 1997) vol. 86, No. 1, pp. 1-12, XP000929450.
Gu et al., "Synthesis of bone resorption inhibitor amino-bisphosphonates and their sodium salts," Zhongguo Yaowu Huaxue Zazhi (Chinese J. Med. Chem.) (Mar. 2000) vol. 10, No. 1, pp. 49-50, XP009057402.
Perry's Chemical Engineer's Handbook, pp. 20-54 to 20-57 (Sixth Edition 1984).
Szabo C. M. et al., "Inhibition of Geranylgeranyl Diphosphate Synthase by Bisphosphonates and Diphosphates: A Potential Route to New Bone Antiresorption and Antiparasitic Agents," J. Med. Chem. (May 23, 2002) vol. 45, No. 11, pp. 2185-2196, XP009057401.
Widler, L. et al., "Highly Potent Geminal Bisphosphonates. From Pamidronate Disodium (Aredia) to Zoledronic Acid (Zometa)," J. Med. Chem. (Aug. 15, 2002) vol. 45, No. 17, pp. 3721-3738, XP001164243.
International Search Report of Application No. PCT/US2005/022410, dated Dec. 22, 2005.

* cited by examiner

*Primary Examiner*—Daniel M Sullivan
*Assistant Examiner*—Chukwuma O Nwaonicha
(74) *Attorney, Agent, or Firm*—Kenyon & Kenyon LLP

(57) ABSTRACT

Provided are novel crystalline and amorphous forms of ibandronic acid, methods for their preparation, and pharmaceutical compositions containing them. Also provided are methods for purifying and assaying ibandronic acid in any crystalline form (or amorphous).

9 Claims, 14 Drawing Sheets

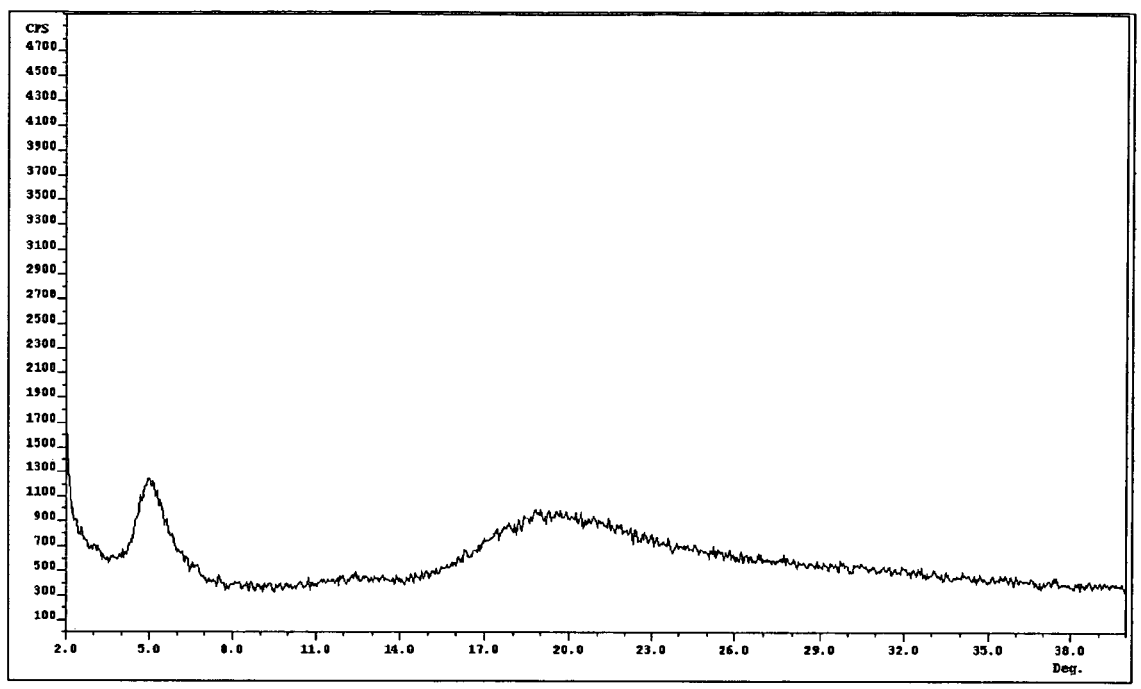
Figure 1: X-Ray powder diffractogram of amorphous form Ibandronic acid

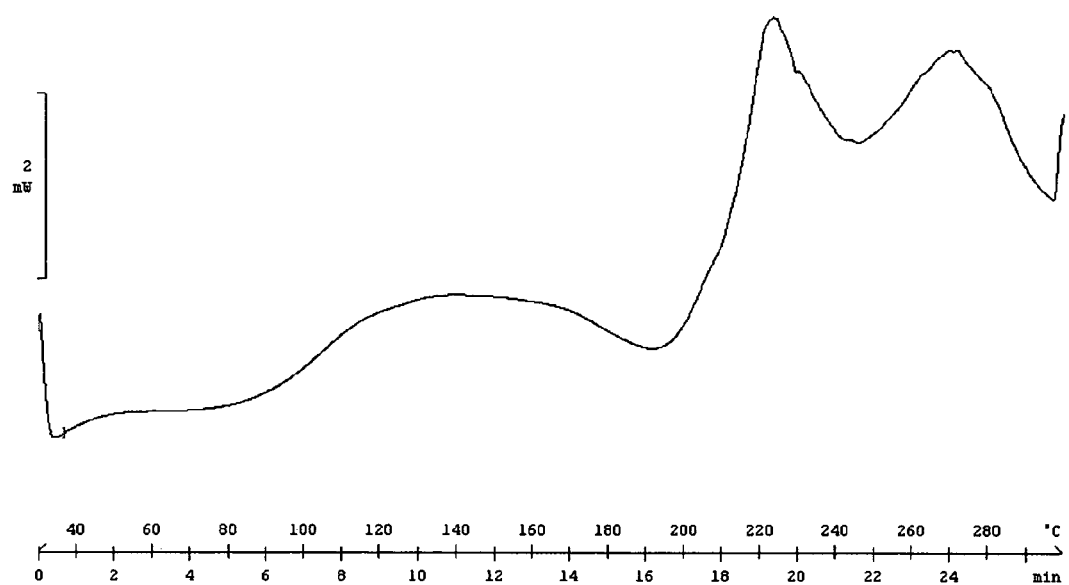
Figure 2: DSC curve of amorphous form Ibandronic acid

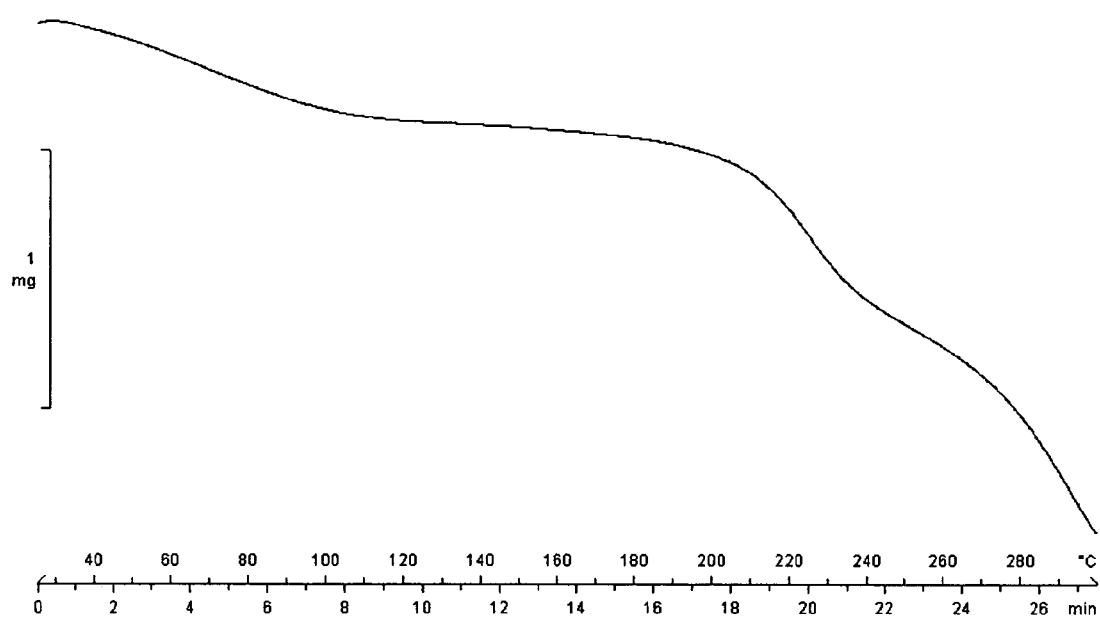
Figure 3: TGA curve of amorphous form Ibandronic acid

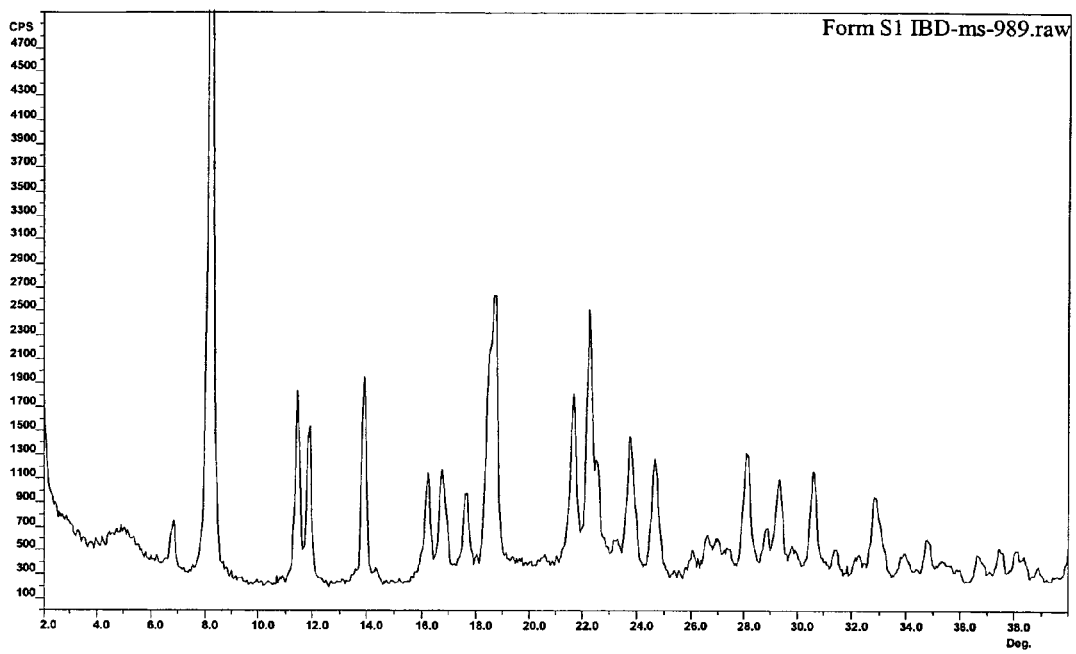
Figure 4: X-Ray powder diffractogram of Form S1 Ibandronic acid

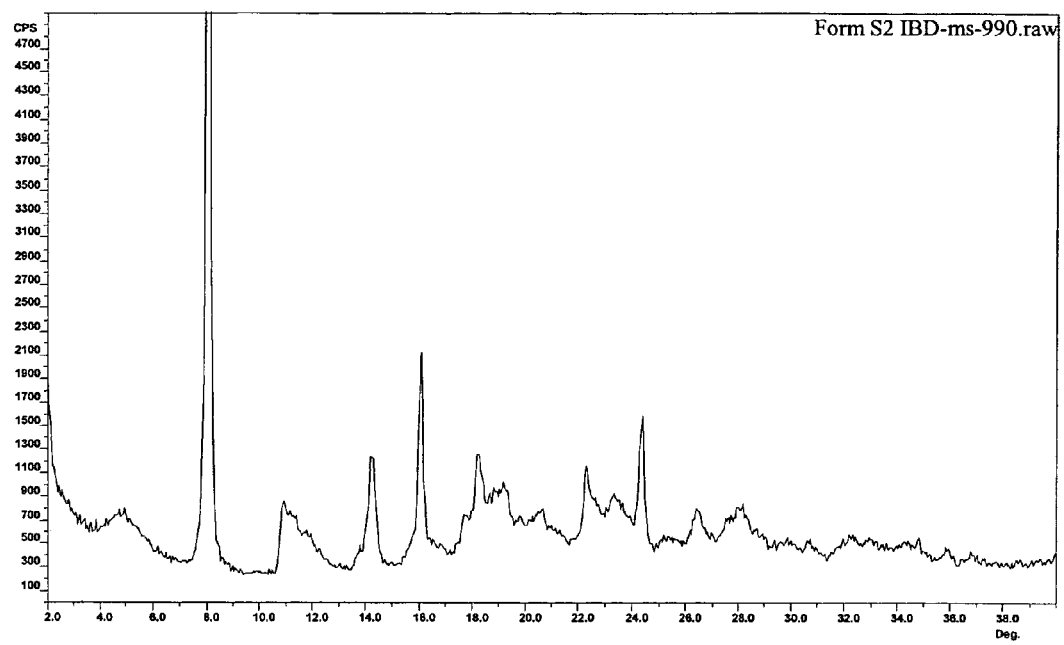
Figure 5: X-Ray powder diffractogram of Form S2 Ibandronic acid

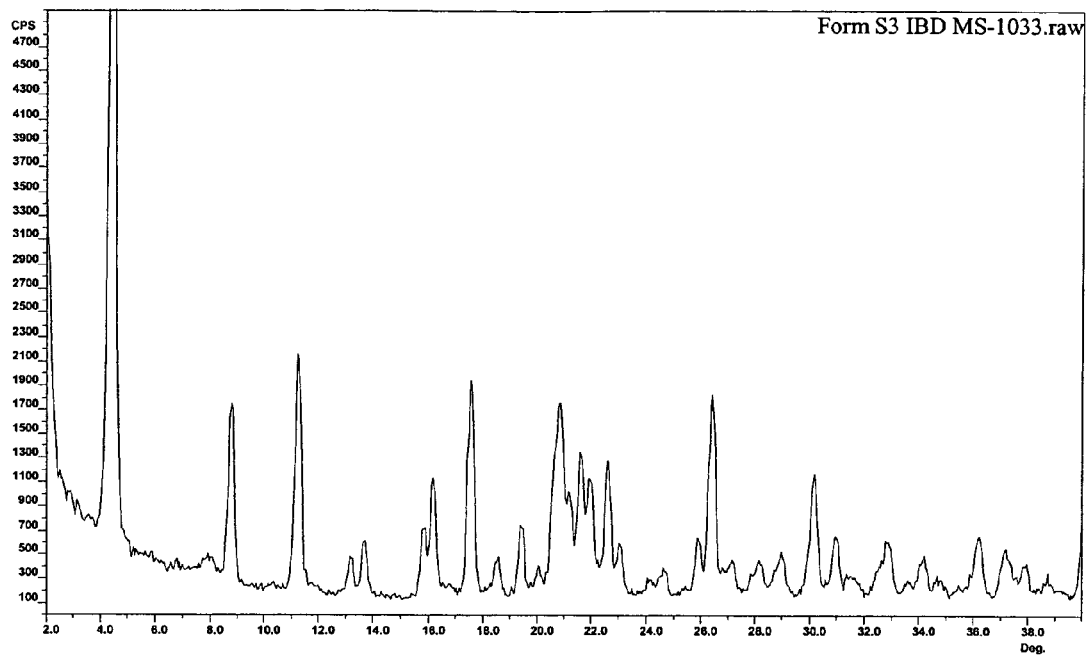
Figure 6: X-Ray powder diffractogram of Form S3 Ibandronic acid

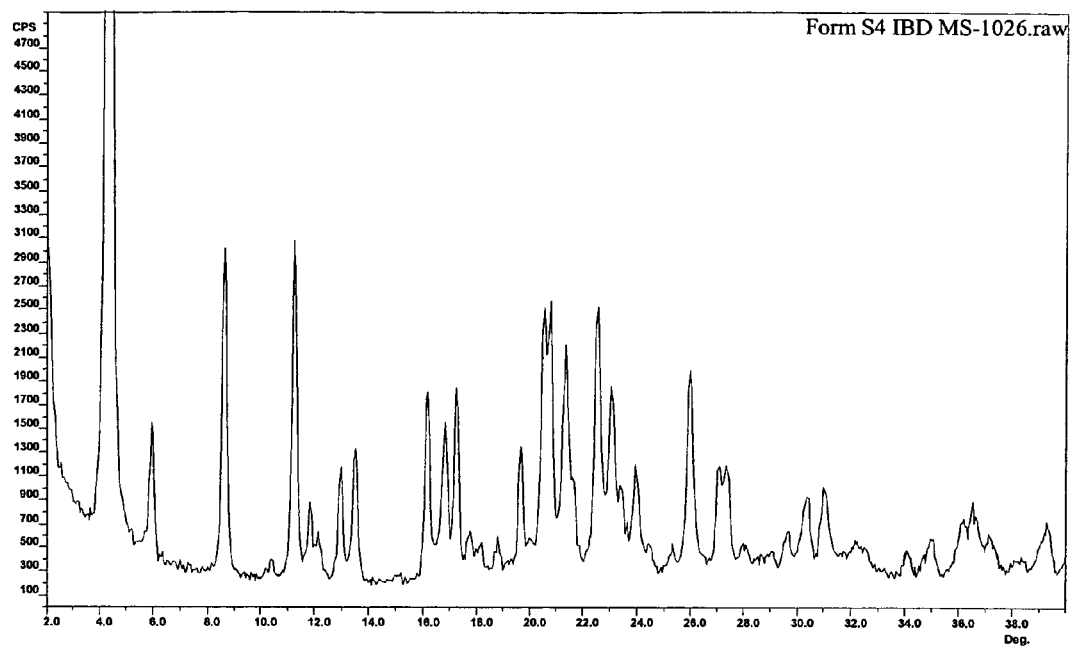
Figure 7: X-Ray powder diffractogram of Form S4 Ibandronic acid

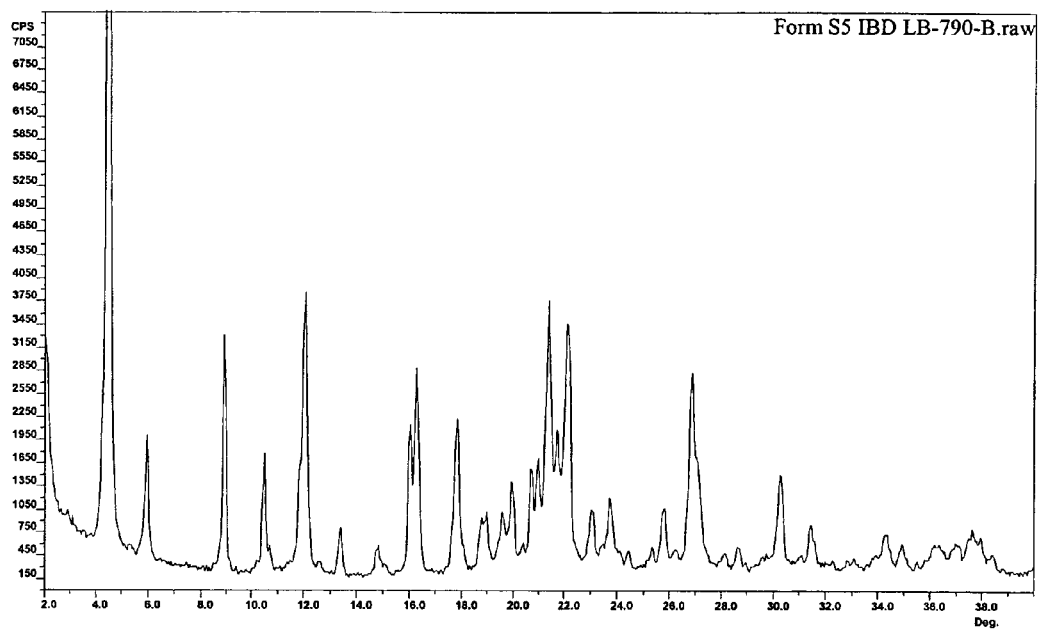
Figure 8: X-Ray powder diffractogram of Form S5 Ibandronic acid

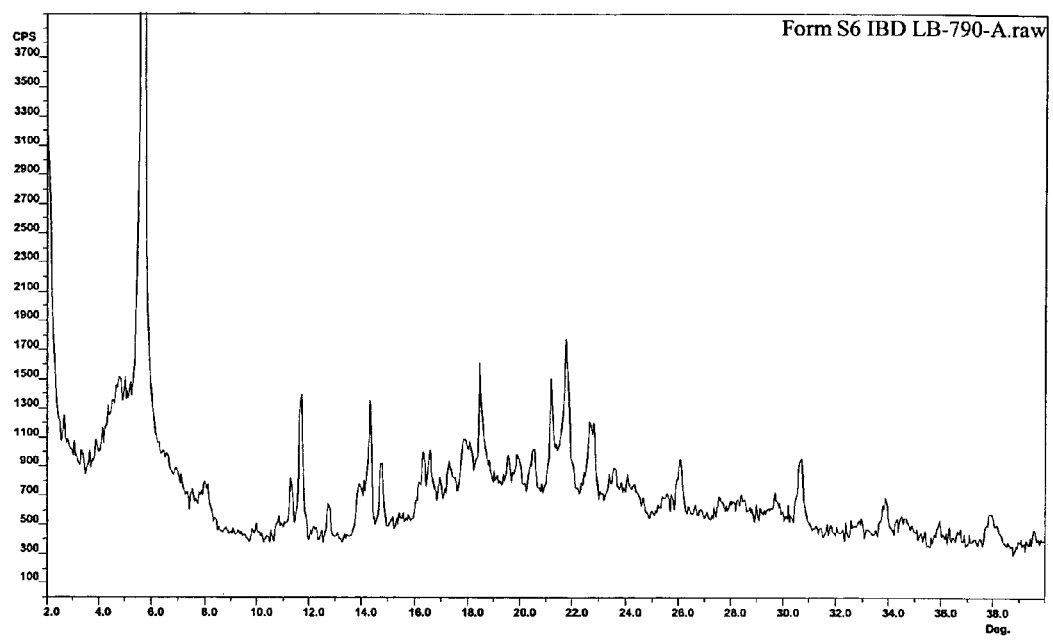
Figure 9: X-Ray powder diffractogram of Form S6 Ibandronic acid

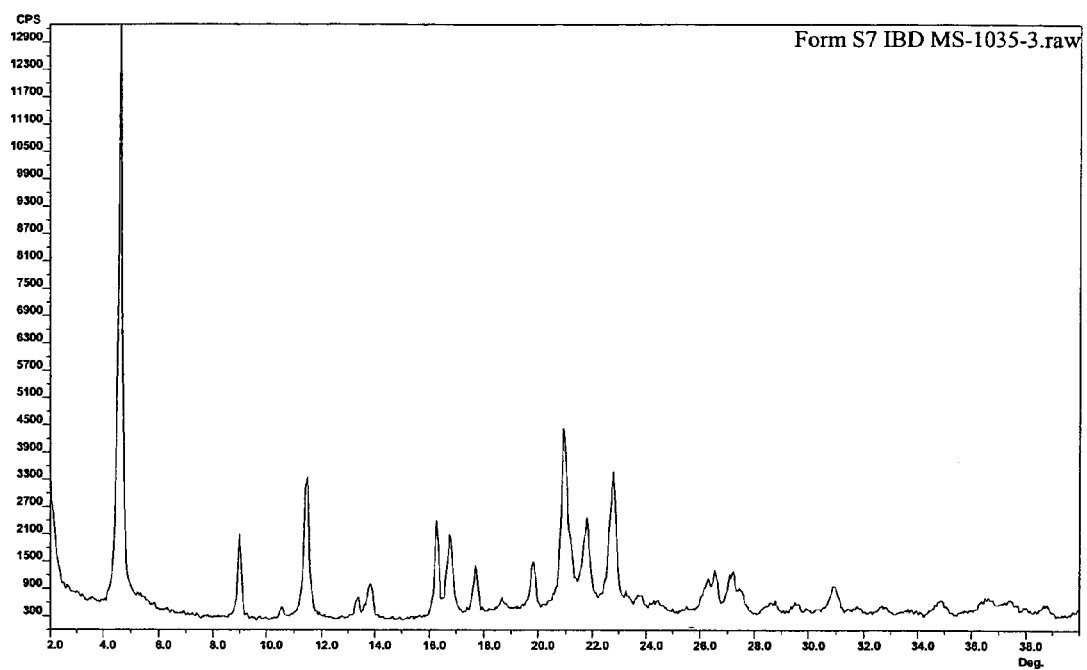
Figure 10: X-Ray powder diffractogram of Form S7 Ibandronic acid

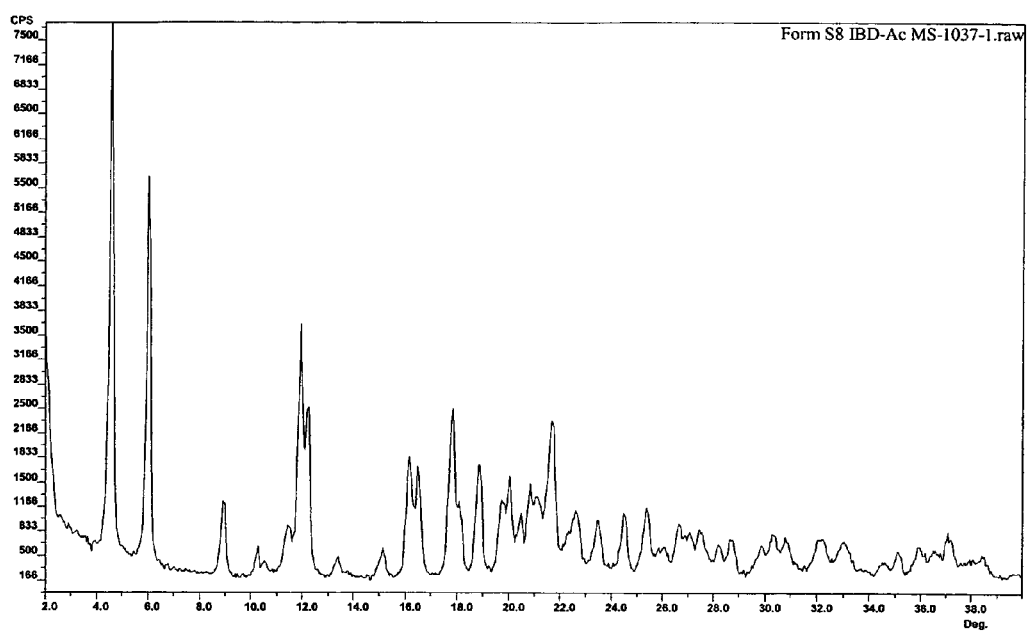
Figure 11: X-Ray powder diffractogram of Form S8 Ibandronic acid

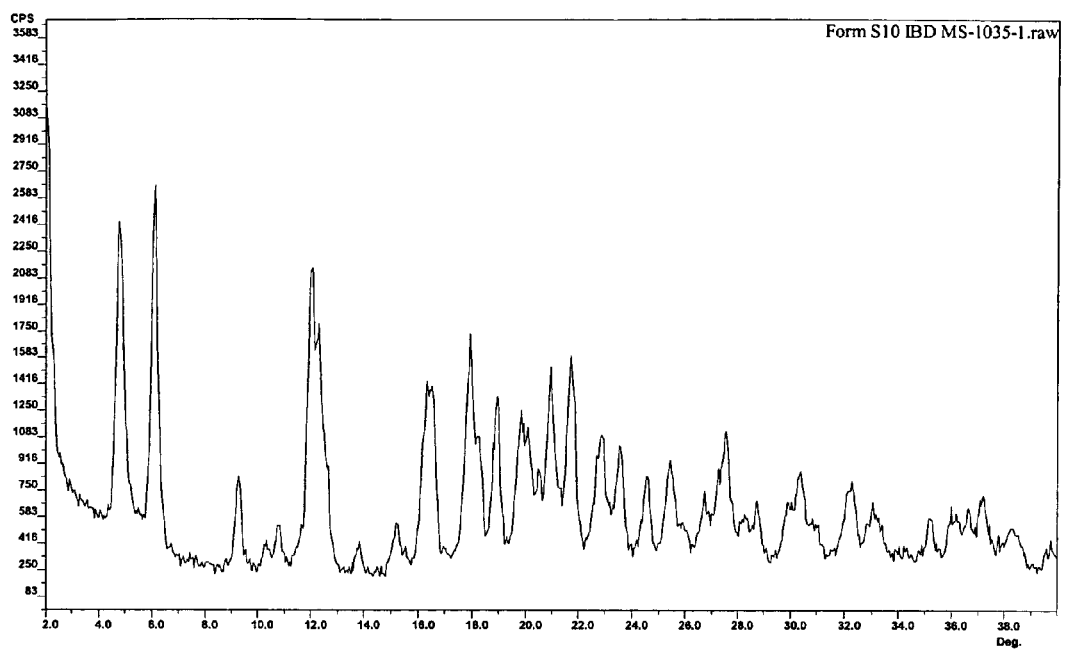
Figure 12: X-Ray powder diffractogram of Form S10 Ibandronic acid

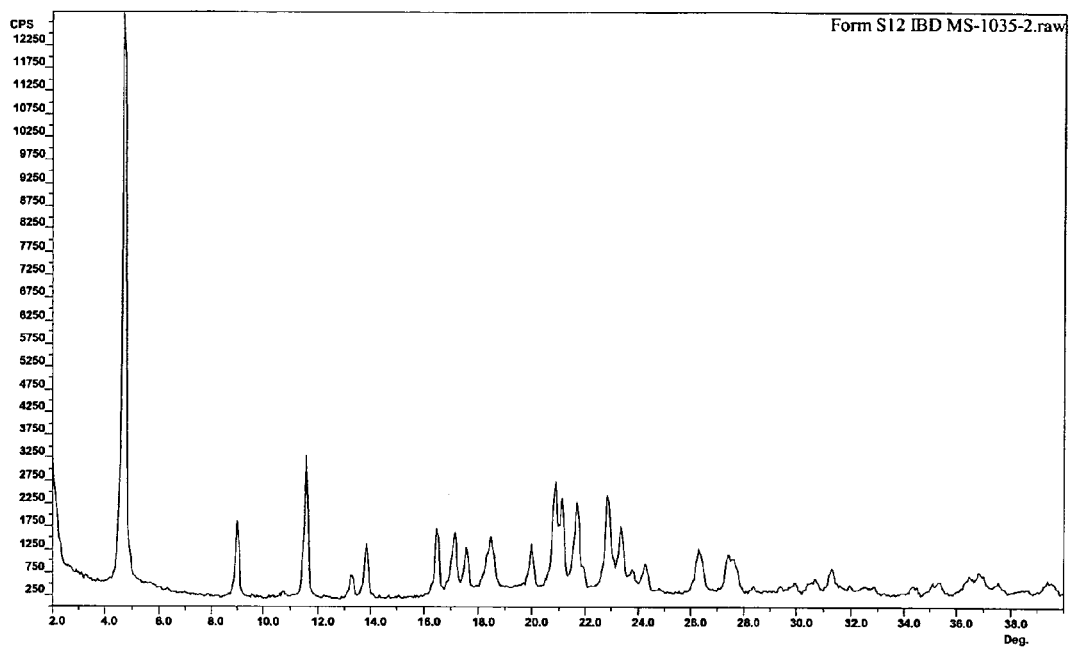
Figure 13: X-Ray powder diffractogram of Form S12 Ibandronic acid

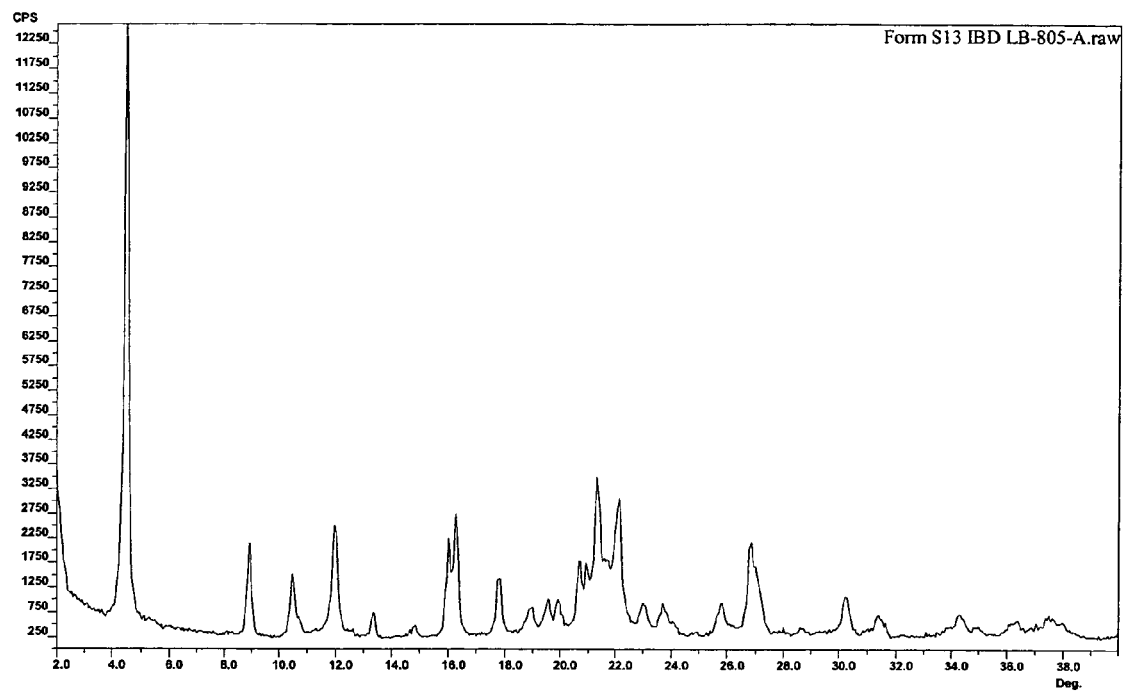
Figure 14: X-Ray powder diffractogram of Form S13 Ibandronic acid

SOLID AND CRYSTALLINE IBANDRONIC ACID

RELATED APPLICATIONS

This application is a continuation of prior application U.S. Ser. No. 11/331,995, filed Jan. 12, 2006, now abandoned which is continuation of application U.S. Ser. No. 11/165,481 filed Jun. 22, 2005, now abandoned which claims the benefit of the 23 Jun. 2004 filing date of U.S. Provisional Patent Application 60/582,500, of the 18 Oct. 2004 filing date of U.S. Provisional Patent Application 60/620,016 and the benefit of the Jun. 16, 2005 filing date of the U.S. Provisional Patent Application 60/690,868. The contents of all of which are incorporated herein by reference.

BACKGROUND OF THE INVENTION

Ibandronate Sodium is a third-generation nitrogen-containing bisphosphonate characterized by an aliphatic tertiary amine side chain.

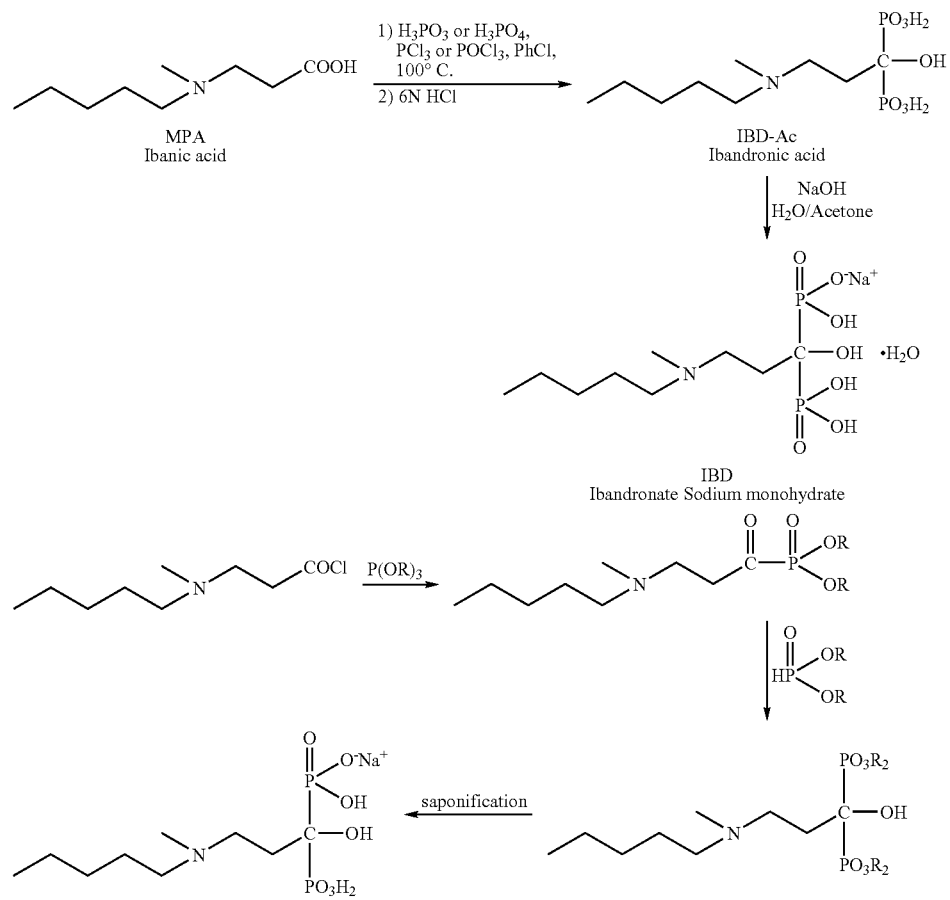

The preparation of ibandronic acid monosodium salt is described in, for example, U.S. Pat. No. 4,927,814. The '814 patent describes the following schemes:

Ibandronate Sodium is a white crystalline powder. The free acid has MW 319.23 (CAS No.: 114084-78-5). The monosodium salt (anhydrous) of the acid has MW 341.23 (CAS No.: 138844-81-2). The monosodium salt monohydrate has MW 359.23 (CAS No.: 138926-19-9).

The preparation of ibandronic acid is taught in U.S. Pat. No. 4,927,814, wherein an ion-exchange chromatography is used in work-up. The present inventors repeated the procedure described in the '814 patent. No solid material was obtained, but an oily precipitate was the crude product. The skilled artisan knows that solids are easier to manipulate than oils. Clearly there is a need for a method of making a solid ibandronic acid.

The monosodium salt of ibandronic acid is marketed under the trade name Boniva®. Boniva® was developed by Hoffmann-La Roche for the treatment of bone disorders such as: hypercalcaemia of malignancy, osteolysis, Paget's disease, osteoporosis and metastatic bone disease. Boniva® is also marketed in Europe under the name Bondronat for cancer-related bone complications. Bondronat is available in ampoule with 1 ml concentrate for solution for infusion contains 1.125 mg of Ibandronic acid monosodium salt monohydrate, corresponding to 1 mg of ibandronic acid.

Ibandronic acid can be used as an intermediate in the process for the preparation of Ibandronate sodium.

The discovery of new polymorphic forms of a pharmaceutically useful compound provides a new opportunity to improve the performance characteristics of a pharmaceutical product. It enlarges the repertoire of materials that a formulation scientist has available for designing, for example, a pharmaceutical dosage form of a drug with a targeted release profile or other desired characteristic. There is a need in the art for polymorphic forms of ibandronic acid.

SUMMARY OF THE INVENTION

In one aspect, the present invention provides amorphous ibandronic acid.

In another aspect, the present invention provides a method of preparing amorphous ibandronic acid that includes the step of isolating amorphous ibandronic acid from an aqueous solution of ibandronic acid which isolating step is selected from a vacuum evaporation step or a lyophilization step.

In still a further aspect, the present invention relates to a method of making amorphous ibandronic comprising the step of spray drying an aqueous solution of ibandronic acid.

In yet another aspect, the present invention provides solid ibandronic acid.

In one aspect, the present invention provides a process for preparing solid Ibandronic acid comprising the steps of:
a) combining, at a temperature of about 72° C. to about 78° C., a halo-phosphorous compound and phosphorous acid with N-methyl-N-pentyl propionic acid hydrochloride in a diluent to obtain a reaction mixture;
b) maintaining the reaction mixture, while heating to a temperature of about 80° C. to about 100° C.;
c) further combining the reaction mixture with water, whereby two phases, one aqueous and one nonaqueous, are obtained;
d) separating the two phases obtained;
e) maintaining the aqueous phase at a temperature of about 95° C. to about 100° C.;
f) evaporating the aqueous phase to obtain a residue;
g) combining an alcohol with the residue to obtain whereby a suspension is obtained; and
h) recovering solid ibandronic acid from the suspension, for example by filteration or centrifugation; and optionally, drying the recovered solid ibandronic acid The residue of step f) may be dissolved in water prior to the addition of the alcohol in step g). After the addition of the alcohol, the reaction mixture may be heated in order to facilitate the formation of the precipitate.

In another aspect, the present invention provides crystalline ibandronic acid in several crystalline forms and hydrates and solvates, especially alcoholates, thereof. The present invention also provides ibandronic acid alcoholates.

In yet another aspect, the present invention provides a solid crystalline form of ibandronic acid, denominated form S1, characterized by a powder X-ray diffraction pattern having reflections at about 8.2, 11.5, 11.9, 13.9, 18.6 and 22.2±0.2 deg. 2-theta. The present invention further provides processes for preparing ibandronic acid form S1.

In one aspect, the present invention provides a solid crystalline form of ibandronic acid, denominated form S2, characterized by a powder X-ray diffraction pattern having reflections at about 8.1, 14.2, 16.1, 18.2 and 24.4±0.2 deg. 2-theta. The present invention further provides a process for preparing ibandronic acid form S2.

In another aspect, the present invention provides a solid crystalline form of ibandronic acid, denominated form S3, characterized by a powder X-ray diffraction pattern having reflections at about 4.4, 8.8, 11.3, 17.6 and 26.4±0.2 deg. 2-theta. The present invention further provides a process for preparing ibandronic acid form S3.

In yet another aspect, the present invention provides a solid crystalline form of ibandronic acid, denominated form S4, characterized by a powder X-ray diffraction pattern having reflections at about 4.4, 8.6, 11.2, 17.3, 20.8, 22.5 and 26.0±0.2 deg. 2-theta. The present invention further provides a process for preparing ibandronic acid form S4.

In one aspect, the present invention provides a solid crystalline form of ibandronic acid, denominated form S5, characterized by a powder X-ray diffraction pattern having reflections at about 4.5, 8.9, 12.0, 16.0, 16.3, 21.4, 22.1 and 26.9±0.2 deg. 2-theta. The present invention further provides processes for preparing ibandronic acid form S5.

In another aspect, the present invention provides a solid crystalline form of ibandronic acid, denominated form S6, characterized by a powder X-ray diffraction pattern having reflections at about 5.7, 11.7, 14.3, 18.5, 21.2 and 21.7±0.2 deg. 2-theta. The present invention further provides processes for preparing ibandronic acid form S6.

In yet another aspect, the present invention provides a solid crystalline form of ibandronic acid, denominated form S7, characterized by a powder X-ray diffraction pattern having reflections at about 4.6, 11.5, 16.3, 16.8, 21.0 and 22.8±0.2 deg. 2-theta. The present invention further provides processes for preparing ibandronic acid form S7.

In one aspect, the present invention provides a solid crystalline form of ibandronic acid, denominated form S8, characterized by a powder X-ray diffraction pattern having reflections at about 4.5, 6.0, 11.9, 12.3, 16.2, 17.8 and 21.7±0.2 deg. 2-theta. The present invention further provides processes for preparing ibandronic acid form S8.

In another aspect, the present invention provides a solid crystalline form of ibandronic acid, denominated form S10, characterized by a powder X-ray diffraction pattern having reflections at about 4.8, 6.1, 12.0, 12.3, 16.4, 18.0 and 21.7±0.2 deg. 2-theta. The present invention further provides processes for preparing ibandronic acid form S10.

In yet another aspect, the present invention provides a solid crystalline form of ibandronic acid, denominated form S12, characterized by a powder X-ray diffraction pattern having reflections at about 4.7, 9.0, 11.6, 20.9, 21.1, 21.7, 22.9 and 26.3±0.2 deg. 2-theta. The present invention further provides a process for preparing ibandronic acid form S5.

In one aspect, the present invention provides a solid crystalline form of ibandronic acid, denominated form S13, characterized by a powder X-ray diffraction pattern having reflections at about 4.5, 8.9, 12.0, 16.0, 16.3, 21.3 and 22.1±0.2 deg. 2-theta. The present invention further provides processes for preparing ibandronic acid form S13.

In another aspect, the present invention provides a process for purifying Ibandronic acid from inorganic impurities by crystallization from an organic solvent selected from the group consisting of $C_{2-4}$ alcohols and acetonitrile.

In yet another aspect, the present invention provides a HPLC method of assaying ibandronic acid comprising the steps of: providing a sample solution of a sample of ibandronic acid in a diluent, loading the sample solution (ca. 50 μL) onto a 250×4.1 mm, Hamilton type PRP-X100 anion exchange column, eluting the sample from the column at 2.0 ml/min. with an eluent including nitric acid ($HNO_3$: 35 vol-%), potassium nitrate ($KNO_3$: 45 vol-%) and ethanol (20 vol-%), and measuring the ibandronic acid content of the eluent at 240 nm wavelength with a UV detector to identify the relevant fractions.

In still a further aspect, the present invention provides A process for purifying ibandronic acid from inorganic impurities comprising the steps of: providing a solution of ibandronic acid containing inorganic impurities in water or methanol; and b) combining the solution with a $C_2$-$C_4$ alcohol, especially wherein the $C_{2-4}$ alcohol is selected from the group consisting of ethanol, 1-propanol, isopropanol (IPA) and tert-butanol whereby ibandronic acid precipitates.

BRIEF DESCRIPTION OF THE FIGURES

FIG. 1 illustrates an x-ray diffraction diagram of amorphous ibandronic acid.

FIG. 2 illustrates a DSC thermogram of amorphous ibandronic acid.

FIG. 3 illustrates a TGA thermogram of ibandronic acid.

FIG. 4 illustrates an x-ray diffraction diagram of ibandronic acid form S1.

FIG. 5 illustrates an x-ray diffraction diagram of ibandronic acid form S2.

FIG. 6 illustrates an x-ray diffraction diagram of ibandronic acid form S3.

FIG. 7 illustrates an x-ray diffraction diagram of ibandronic acid form S4.

FIG. 8 illustrates an x-ray diffraction diagram of ibandronic acid form S5.

FIG. 9 illustrates an x-ray diffraction diagram of ibandronic acid form S6.

FIG. 10 illustrates an x-ray diffraction diagram of ibandronic acid form S7.

FIG. 11 illustrates an x-ray diffraction diagram of ibandronic acid form S8.

FIG. 12 illustrates an x-ray diffraction diagram of ibandronic acid form S10.

FIG. 13 illustrates an x-ray diffraction diagram of ibandronic acid form S12.

FIG. 14 illustrates an x-ray diffraction diagram of ibandronic acid form S13.

DETAILED DESCRIPTION OF THE INVENTION

The present invention provides processes which utilize halo-phosphorous compounds. Such compounds include, but are not limited to, phosphorous trichloride, phosphorous oxychloride, phosphorous pentachloride, phosphorous tribromide, phosphorous oxybromide, phosphorous pentabromide.

In particular embodiments of the present invention, $C_2$-$C_4$ alcohols are used. The $C_2$-$C_4$ alcohols have the general structure ROH wherein R is a linear or branched alkyl group having 2 to 4 carbon atoms. Ethanol, n-propanol (1-propanol), iso-propanol (2-propanol, IPA), and t-butanol (2-methylpropan-2-ol) are preferred C2-C4 alcohols.

The present invention also provides processes that, in particular embodiments, utilize strong acids which do not act as oxidants for amino-phosphonic acids. Such non-oxidizing acids include, but are not limited to, para-toluene sulfonic acid, HCl, HBr, and trichloroacetic acid.

The present invention provides amorphous ibandronic acid. Amorphous ibandronic acid has an x-ray diffraction diagram not unexpected for an essentially amorphous solid. FIG. 1 shows a representative x-ray diffraction diagram of amorphous ibandronic acid.

FIG. 2 shows a representative thermogram from differential scanning calorimetry (DSC) for amorphous ibandronic acid. The DSC thermogram does not exhibit any feature that can be clearly associated with a first-order transition like crystal melting.

FIG. 3 shows a representative thermogram from thermogravimetric analysis (TGA).

Amorphous ibandronic acid can be prepared by a method that includes an isolation step. An isolation step is a step (procedure) in which a solvent, for example water is removed from a solution of ibandronic acid and can be called a "water-removal" step. This step comprises isolation of amorphous ibandronic acid from a solution of ibandronic acid in a solvent selected from the group consisting of acetonitrile (ACN), dimethylsulfoxide (DMSO), methanol, and water. Preferably, the solvent is water. The isolation step can be a vacuum evaporation (i.e. concentration) step, a lyophilization step, or a spray drying step.

The term "spray drying" broadly refers to processes involving breaking up liquid mixtures into small droplets (atomization) and rapidly removing solvent from the mixture. In a typical spray drying apparatus, there is a strong driving force for evaporation of solvent from the droplets, which may be provided by providing a drying gas. Spray drying processes and equipment are described in Perry's Chemical Engineer's Handbook, pgs. 20-54 to 20-57 (Sixth Edition 1984).

By way of non-limiting example only, the typical spray drying apparatus comprises a drying chamber, atomizing means for atomizing a solvent-containing feed into the drying chamber, a source of drying gas that flows into the drying chamber to remove solvent from the atomized-solvent-containing feed, an outlet for the products of drying, and product collection means located downstream of the drying chamber. Examples of such apparatuses include Niro Models PSD-1, PSD-2 and PSD-4 (Niro A/S, Soeborg, Denmark). Typically, the product collection means includes a cyclone connected to the drying apparatus. In the cyclone, the particles produced during spray drying are separated from the drying gas and evaporated solvent, allowing the particles to be collected. A filter may also be used to separate and collect the particles produced by spray drying. The process of the invention is not limited to the use of such drying apparatuses as described above.

Spray drying may be performed in a conventional manner in the processes of the present invention (see, e.g., Remington: The Science and Practice of Pharmacy, 19th Ed., vol. II, pg. 1627, herein incorporated by reference). The drying gas used in the invention may be any suitable gas, although inert gases such as nitrogen, nitrogen-enriched air, and argon are preferred. Nitrogen gas is a particularly preferred drying gas for use in the process of the invention. The amorphous ibandronic acid product produced by spray drying may be recovered by techniques commonly used in the art, such as using a cyclone or a filter. Spray drying of ibandronic acid from a solution of ibandronic acid in water results in amorphous ibandronic acid.

The present invention also provides solid ibandronic acid. When intermediate compounds are Solid substances rather than liquid, it enables the possibility of isolating and purifying the intermediate by crystallization thereby improving the quality of the final product.

The present invention also provides solid ibandronic acid. Solid ibandronic acid can be prepared by a process that includes the steps of:
a) combining, at a temperature of about 70° C. to about 78° C., a halo-phosphorous compound and phosphorous acid with N-methyl-N-pentyl propionic acid hydrochloride in a diluent;
b) maintaining the reaction mixture, while heating to a temperature of about 80° C. to about 100° C.;
c) combining the reaction mixture with water, whereby two phases are obtained;
d) separating the two phases obtained;
e) maintaining the aqueous phase at a temperature of about 95° C. to about 110° C.;
f) evaporating the aqueous phase to obtain a residue;
g) combining a $C_{2-4}$ alcohol or acetone with the reaction mixture to obtain a precipitate; and
h) recovering the precipitate of solid ibandronic acid.

Preferably, the halo-phosphorous compound of step a) is added in small aliquots, especially dropwise. Preferably, the diluent in step a) is selected from the group consisting of silicone oil, toluene and a mixture of toluene and phosphoric acid. Preferably, the temperature in step a) is about 75° C.

Preferably, the mixture in step b) is heated to a temperature of about 80° C. Preferably, the $C_{2-4}$ alcohol in step g) is selected from the group consisting of ethanol, 1-propanol, isopropyl alcohol (IPA) and tert-butanol. Most preferably, the alcohol in step g) is ethanol or IPA. The residue of step f) can be combined with water prior to the addition of the alcohol in step g). After the addition of the $C_{2-4}$ alcohol, the reaction mixture is optionally heated in order to facilitate the formation of the precipitate.

The present invention further provides crystalline ibandronic acid, hydrates and solvates thereof. The present invention also provides ibandronic acid alcoholates. As a general rule, crystalline forms possess the advantage of being readily filterable, easily dried, and stable for extended periods of time without the need for specialized storage conditions.

In another embodiment, the present invention provides a solid crystalline form of ibandronic acid, denominated form S1, characterized by a powder X-ray diffraction pattern having reflections at about 8.2, 11.5, 11.9, 13.9, 18.6 and 22.2±0.2 deg. 2-theta. Solid crystalline ibandronic acid form S1 is further characterized by X-ray powder diffraction pattern having reflections at about 21.6, 23.8, 24.7 and 28.1±0.2 deg. 2-theta. A typical x-ray diffraction diagram for ibandronic acid form S1 is given in FIG. 4. Form S1 can be a hemihydrate.

Ibandronic acid form S1 can be prepared by combining an organic solvent selected from the group consisting of tert-butanol, ethanol, and acetone, with an aqueous solution of ibandronic acid, and maintaining the resulting combination for up to about 24 hours to obtain a precipitate of ibandronic acid form S1. Preferably, the organic solvent is selected from the group consisting of tert-butanol, ethanol and acetone.

Form S1 can be also prepared by combining amorphous ibandronic acid and an organic solvent at a temperature that ranges from room temperature to reflux, and maintaining the reaction mixture for a sufficient time to obtain form S1 in a slurry. Preferably, the organic solvent is selected from the group consisting of tert-butanol, ethanol and acetone.

Ibandronic acid form S1 can also be prepared in a process that includes the steps of dissolving amorphous ibandronic acid in water, adding acetone to obtain in a slurry, and stirring the slurry for a sufficient time to obtain form S1.

Form S1 can be also prepared by a process that includes the steps of:
a) combining, at a temperature of about 70° C. to about 78° C., a halo-phosphorous compound and phosphorous acid with N-methyl-N-pentyl propionic acid hydrochloride in toluene;
b) maintaining the reaction mixture, while heating to a temperature of about 80° C. to about 100° C.;
c) removing the toluene and adding water to the reaction mixture;
d) maintaining the reaction mixture at a reflux temperature;
e) evaporating to obtain a residue;
f) combining ethanol with the residue to obtain a precipitate; and
g) recovering crystalline ibandronic acid form S1.

Preferably, the halo-phosphorous compound of step a) is added in small aliquots, most preferably dropwise. Preferably, the temperature in step a) is about 75° C. Preferably, the reaction mixture in step b) is heated to a temperature of about 80° C.

In a further embodiment, the present invention further provides a solid crystalline form of ibandronic acid, denominated form S2, characterized by a powder X-ray diffraction pattern having reflections at about 8.1, 14.2, 16.1, 18.2 and 24.4±0.2 deg. 2-theta. Solid crystalline ibandronic acid form S2 can be further characterized by X-ray reflections at about 10.9, 19.2, 22.3, 23.3, and 28.2±0.2 deg. 2-theta. A typical x-ray diffraction diagram for ibandronic acid form S2 is given in FIG. 5.

Ibandronic acid form S2 can be prepared by providing a solution of amorphous ibandronic acid in methanol; adding acetonitrile solvent to the solution to obtain a slurry and recovering ibandronic acid form S2.

In a further embodiment, the present invention provides a solid crystalline form of ibandronic acid, denominated form S3, characterized by a powder X-ray diffraction pattern having reflections at about 4.4, 8.8, 11.3, 17.6 and 26.4±0.2 deg. 2-theta. Solid crystalline ibandronic acid form S3 can be further characterized by X-ray reflections at about 21.6, 23.8, 24.7 and 28.1±0.2 deg. 2-theta. A typical x-ray diffraction diagram for ibandronic acid form S3 is given in FIG. 6. Form S3 can exist as a tert-butanolate.

Ibandronic acid form S3 can be prepared by adding tert-butanol, to an aqueous solution of ibandronic acid, and maintaining the resulting mixture for at least about 24 hours or more to obtain form S3.

In another embodiment, the present invention provides a solid crystalline form of ibandronic acid, denominated Form S4, characterized by a powder X-ray diffraction pattern having reflections at about 4.4, 8.6, 11.2, 17.3, 20.8, 22.5 and 26.0±0.2 deg. 2-theta. Solid crystalline ibandronic acid Form S4 can be further characterized by X-ray reflections at about 16.2, 20.5 and 21.3±0.2 deg. 2-theta. A typical x-ray diffraction diagram for ibandronic acid Form S4 is given in FIG. 7. Form S4 can be a propanolate.

Ibandronic acid Form S4 can be prepared by combining at room temperature an aqueous solution of ibandronic acid and 1-propanol until precipitation occurs, and isolating Form S4. Preferably the combination is stirred for at least about 3 hours. Optionally, the combination is heated to a reflux temperature, in order to obtain a stirrable mixture, which is then cooled to room temperature.

In yet another embodiment, the present invention provides a solid crystalline form of ibandronic acid, denominated Form S5, characterized by a powder X-ray diffraction pattern having reflections at about 4.5, 8.9, 12.0, 16.0, 16.3, 21.4, 22.1 and 26.9±0.2 deg. 2-theta. Solid crystalline ibandronic acid Form S1 can be further characterized by X-ray reflections at about 5.9, 10.5 and 17.8+0.2 deg. 2-theta. A typical x-ray diffraction diagram for ibandronic acid Form S5 is given in FIG. 8. Form S5 exists as a hemihydrate or an iso-propanolate (isopropyl alcohol solvate).

Ibandronic acid Form S5 can be prepared by a process that includes the steps of:
a) combining, at a temperature of about 70° C. to about 78° C., a halo-phosphorous compound and phosphorous acid with N-methyl-N-pentyl propionic acid hydrochloride in a silicone oil to obtain a reaction mixture;
b) heating the reaction mixture to a temperature of about 80° C. to about 100° C., and maintaining while stirring;
c) combining water with the reaction mixture, whereby two phases, one aqueous, one nonaqueous, are obtained;
d) separating the two phases obtained;
e) maintaining the aqueous phase at a reflux temperature;
f) evaporating the aqueous phase to obtain a residue;
g) adding IPA to the residue,
h) maintaining the reaction mixture for 24 hours or more to obtain a precipitate; and
i) recovering crystalline ibandronic acid Form S5.

Preferably, the halo-phosphorous compound of step a) is added in small aliquots, most preferably dropwise. Preferably, the temperature in step a) is about 75° C. Preferably, the reaction mixture in step b) is heated to a temperature of about 80° C. The residue of step f) can be dissolved in water prior to the addition of the IPA in step g). Optionally, the mixture of the IPA and the residue is cooled to facilitate precipitation.

Form S5 can be also prepared by a process including the steps of:
a) combining, at a temperature of about 70° C. to about 78° C., a halo-phosphorous compound and phosphorous acid with N-methyl-N-pentyl propionic acid hydrochloride in toluene to form a multi-phase reaction mixture;
b) maintaining the reaction mixture, while heating to a temperature of about 80° C. to about 100° C.;
c) removing the toluene, especially by decanting or any other liquid-liquid separation technique, and combining water with the reaction mixture;
d) maintaining the reaction mixture at a reflux temperature, and evaporating to obtain a residue;
e) adding IPA to the residue to obtain a slurry; and
f) recovering crystalline ibandronic acid Form S5 from the slurry.

Preferably, the temperature in step a) is about 75° C. Preferably, the reaction mixture in step b) is heated to a temperature of about 80° C. Preferably, the halo-phosphorous compound of step a) is added slowly, in small aliquots, most preferably dropwise. In addition to water, a strong acid which does not act as oxidant for amino-phosphonic acids may be added to the reaction mixture of step c). The acid is thought to hydrolize the phosphorous intermediates that form during the previous steps. Preferably, the acid is concentrated HCl.

Ibandronic acid Form S5 can be prepared by stirring a combination of amorphous ibandronic acid with an organic solvent selected from the group consisting of tetrahydrofuran (THF) and ethanol; and recovering Form S5. The combination is optionally heated to reflux temperature.

In another embodiment, the present invention provides a solid crystalline form of ibandronic acid, denominated Form S6, characterized by a powder X-ray diffraction pattern having reflections at about 5.7, 11.7, 14.3, 18.5, 21.2 and 21.7±0.2 deg. 2-theta. Solid crystalline ibandronic acid Form S6 can be further characterized by X-ray reflections at about 14.8, 22.7, 22.8 and 30.6±0.2 deg. 2-theta. A typical x-ray diffraction diagram for ibandronic acid form S6 is given in FIG. 9. Form S6 can exist as a hemihydrate, tert-butanolate, or a mixture of both.

Ibandronic acid Form S6 can be prepared by a process including the steps of:
a) combining, at a temperature of about 70° C. to about 78° C., a halo-phosphorous compound and phosphorous acid with N-methyl-N-pentyl propionic acid hydrochloride in a silicone oil to obtain a reaction mixture;
b) heating the reaction mixture to a temperature of about 80° C. to about 100° C., and maintaining while stirring;
c) combining water with the reaction mixture, whereby two phases, one aqueous, one nonaqueous, are obtained;
d) separating the two phases obtained;
e) maintaining the aqueous phase at a reflux temperature;
f) evaporating the aqueous phase to obtain a residue;
g) dissolving the residue in water, followed by the addition of tert-butanol to obtain a precipitate; and
h) recovering crystalline ibandronic acid Form S6.

Preferably, the halo-phosphorous compound of step a) is added slowly, in small aliquots, especially dropwise. Preferably, the temperature in step a) is about 75° C. Preferably, the reaction mixture in step b) is heated to a temperature of about 80° C.

Form S6 can be also prepared by a process that includes the steps of:
a) combining, at a temperature of about 70° C. to about 78° C., a halo-phosphorous compound and phosphorous acid with N-methyl-N-pentyl propionic acid hydrochloride in toluene to obtain a multiphase reaction mixture;
b) maintaining the reaction mixture, while heating to a temperature of at least about 95° C.;
c) separating the toluene by decantation or any technique for liquid-liquid separation, and adding an acid to the reaction mixture;
d) maintaining the reaction mixture at a reflux temperature, and evaporating to obtain a residue;
e) dissolving the residue in water, followed by the addition of tert-butanol to obtain a precipitate;
f) recovering crystalline ibandronic acid Form S6.

Preferably, the halo-phosphorous compound of step a) is added dropwise. Preferably, the acid in step c) is a strong acid which does not act as oxidant for amino-phosphonic acids. Most preferably, the acid in step c) is concentrated HCl. Preferably, the temperature in step a) is about 75° C.

In another embodiment, the present invention provides a solid crystalline form of ibandronic acid, denominated Form S7, characterized by a powder X-ray diffraction pattern having reflections at about 4.6, 11.5, 16.3, 16.8, 21.0 and 22.8±0.2 deg. 2-theta. Solid crystalline ibandronic acid Form S7 can be further characterized by X-ray reflections at about 9.0, 17.7, 19.8 and 21.8±0.2 deg. 2-theta. A typical x-ray diffraction diagram for ibandronic acid Form S7 is given in FIG. 10. Form S7 can exist as a hemihydrate, a 1-propanolate, or an iso-propanolate.

Ibandronic acid Form S7 can be prepared by a process including the steps of:
a) combining, at a temperature of about 70° C. to about 78° C., a halo-phosphorous compound and phosphorous acid with N-methyl-N-pentyl propionic acid hydrochloride in a silicone oil to obtain a reaction mixture;
b) heating the reaction mixture to a temperature of about 80° C. to about 100° C., and maintaining while stirring;

c) combining the reaction mixture with water, whereby two phases, one aqueous, one nonaqueous, are obtained;
d) separating the two phases obtained;
e) maintaining the aqueous phase at a reflux temperature;
f) concentrating the aqueous phase to obtain a residue;
g) adding IPA or n-propanol ? to the residue,
h) maintaining the reaction mixture for less than 24 hours to obtain a precipitate; and
i) recovering crystalline ibandronic acid Form S7.

Preferably, the halo-phosphorous compound of step a) is added slowly, in small aliquots, most preferably dropwise. Preferably, the temperature in step a) is about 70° C. Preferably, the reaction mixture in step b) is heated to a temperature of about 80° C.

Form S7 can be also prepared by a process including the steps of:
a) combining, at a temperature of about 70° C. to about 78° C., a halo-phosphorous compound and phosphorous acid with N-methyl-N-pentyl propionic acid hydrochloride in toluene to obtain a multiphase reaction mixture;
b) maintaining the reaction mixture, while heating to a temperature of about 80° C. to about 100° C.;
c) separating the toluene, for example by decanting or any technique for liquid-liquid separation, and combining water with the reaction mixture;
d) maintaining the reaction mixture at a reflux temperature, and concentrating to obtain a residue;
e) combining 1-propanol with the residue obtain a precipitate;
f) recovering crystalline ibandronic acid Form S7.

Preferably, the halo-phosphorous compound of step a) is added slowly, in small aliquots, most preferably dropwise. Preferably, the temperature in step a) is about 75° C. Preferably, the reaction mixture in step b) is heated to a temperature of about 80° C.

In yet another embodiment, the present invention provides a solid crystalline form of ibandronic acid, denominated Form S8, characterized by a powder X-ray diffraction pattern having reflections at about 4.5, 6.0, 11.9, 12.3, 16.2, 17.8 and 21.7±0.2 deg. 2-theta. Solid crystalline ibandronic acid Form S8 can be further characterized by X-ray reflections at about 9.0, 16.5 and 18.9, ±0.2 deg. 2-theta. A typical x-ray diffraction diagram for ibandronic acid Form S8 is given in FIG. 11. Form S8 can be exist as an ethanolate or an iso-propanolate.

Ibandronic acid Form S8 can be prepared by a process including the steps of:
a) combining, at a temperature of about 70° C. to about 78° C., a halo-phosphorous compound and phosphorous acid with N-methyl-N-pentyl propionic acid hydrochloride in a silicone oil to obtain a reaction mixture;
b) heating the reaction mixture to a temperature of about 80° C. to about 100° C., and maintaining while stirring;
c) combining the reaction mixture with water, whereby two phases, one aqueous, one nonaqueous, are obtained;
d) separating the two phases obtained;
e) maintaining the aqueous phase at a reflux temperature;
f) concentrating the aqueous phase to obtain a residue;
g) adding a $C_{2-4}$ alcohol to the residue to obtain a precipitate; and
h) recovering crystalline ibandronic acid Form S8.

Preferably, the halo-phosphorous compound of step a) is added slowly, in small aliquots, most preferably dropwise. Preferably, the temperature in step a) is about 75° C. Preferably, the reaction mixture in step b) is heated to a temperature of about 80° C. The residue of step f) may be dissolved in water prior to the addition of the $C_{2-4}$ alcohol in step g). Preferably, the $C_{2-4}$ alcohol in step g) is selected from the group consisting of ethanol, 1-propanol and IPA. Most preferably, the $C_{2-4}$ alcohol in step g) is ethanol.

In another embodiment, the present invention provides a solid crystalline form of ibandronic acid, denominated Form S10, characterized by a powder X-ray diffraction pattern having reflections at about 4.8, 6.1, 12.0, 12.3, 16.4, 18.0 and 21.7±0.2 deg. 2-theta. Solid crystalline ibandronic acid Form S10 can be further characterized by X-ray reflections at about 18.9, 20.9 and 22.8±0.2 deg. 2-theta. A typical x-ray diffraction diagram for ibandronic acid Form S10 is given in FIG. 12. Form S10 can exist as an ethanolate.

Ibandronic acid Form S10 can be prepared by a process comprising the steps of:
a) combining, at a temperature of about 70° C. to about 78° C., a halo-phosphorous compound and phosphorous acid with N-methyl-N-pentyl propionic acid hydrochloride in a silicone oil to obtain a reaction mixture;
b) heating the reaction mixture to a temperature of about 80° C. to about 100° C., and maintaining while stirring;
c) combining the reaction mixture with water, whereby two phases, one aqueous, one nonaqueous, are obtained;
d) separating the two phases obtained;
e) maintaining the aqueous phase at a reflux temperature;
f) concentrating the aqueous phase to obtain a residue;
g) adding ethanol to the residue to obtain a slurry; and
h) recovering from the slurry crystalline ibandronic acid Form S10.

Preferably, the halo-phosphorous compound of step a) is added slowly, in small aliquots, most preferably dropwise. Preferably, the reaction mixture in step b) is heated to a temperature of about 80° C. The residue of step f) may be dissolved in water prior to the addition of the ethanol in step g). The reaction mixture in step g) may be seeded with amorphous ibandronic acid following the addition of the ethanol in step g).

In another embodiment, the present invention provides a solid crystalline form of ibandronic acid, denominated Form S12, characterized by a powder X-ray diffraction pattern having reflections at about 4.7, 9.0, 11.6, 20.9, 21.1, 21.7, 22.9 and 26.3±0.2 deg. 2-theta. Solid crystalline ibandronic acid form S12 may be further characterized by X-ray reflections at about 13.8, 17.1 and 18.4±0.2 deg. 2-theta. A typical x-ray diffraction diagram for ibandronic acid Form S12 is given in FIG. 13. Form S12 can be a hemihydrate and/or an isopropanolate.

Ibandronic acid Form S12 can be prepared by a process including the steps of:
a) combining, at a temperature of about 70° C. to about 78° C., a halo-phosphorous compound and phosphorous acid with N-methyl-N-pentyl propionic acid hydrochloride in a silicone oil to obtain a reaction mixture;
b) heating the reaction mixture to a temperature of about 80° C. to about 100° C., and maintaining while stirring;
c) combining water with the reaction mixture, whereby two phases, one aqueous, one nonaqueous, are obtained;
d) separating the two phases obtained;
e) maintaining the aqueous phase at a reflux temperature;
f) concentrating the aqueous phase to obtain a residue;
g) combining the residue with 1-propanol to obtain a precipitate; and
h) recovering crystalline ibandronic acid Form S12.

Preferably, the halo-phosphorous compound of step a) is added slowly, in small aliquots, especially dropwise. Preferably, the temperature in step a) is about 70° C. Preferably, the reaction mixture in step b) is heated to a temperature of about 80° C.

In yet another embodiment, the present invention provides a solid crystalline form of ibandronic acid, denominated Form S13, characterized by a powder X-ray diffraction pattern having reflections at about 4.5, 8.9, 12.0, 16.0, 16.3, 21.3 and 22.1±0.2 deg. 2-theta. Solid crystalline ibandronic acid Form S13 can be further characterized by X-ray reflections at about 10.5, 17.8 and 26.9±0.2 deg. 2-theta. A typical x-ray diffraction diagram for ibandronic acid Form S13 is given in FIG. 14. Form S13 can exist as an isopropanolate.

Ibandronic acid Form S13 can be prepared by a process including the steps of:
a) combining, at a temperature of about 70° C. to about 78° C., a halo-phosphorous compound and phosphorous acid with N-methyl-N-pentyl propionic acid hydrochloride in a silicone oil to obtain a reaction mixture;
b) heating the reaction mixture to a temperature of about 80° C. to about 100° C., and maintaining while stirring;
c) combining the reaction mixture with water, whereby two phases, one aqueous, one nonaqueous, are obtained;
d) maintaining the reaction mixture at a temperature of about 100° C.;
e) separating the two phases obtained;
f) maintaining the aqueous phase at a temperature of about 75° C. to about 100° C.;
g) concentrating the aqueous phase to obtain a residue;
h) adding IPA to the residue to obtain a precipitate; and
i) recovering crystalline ibandronic acid Form S13.

Preferably, the halo-phosphorous compound of step a) is added slowly, in small aliquots, especially dropwise. Preferably, the temperature in step a) is about 75° C. Preferably, the reaction mixture in step b) is heated to a temperature of about 80° C.

Ibandronic acid Form S13 can be also prepared by a process including the steps of:
a) combining, at a temperature of at least about 95° C., a halo-phosphorous compound and phosphorous acid with N-methyl-N-pentyl propionic acid hydrochloride to obtain a reaction mixture;
b) maintaining while stirring the reaction mixture at a temperature of about 95° C. to about 100° C.;
c) combining the reaction mixture with water;
d) cooling the reaction mixture to room temperature and concentrating to obtain a residue;
e) dissolving the residue in water, followed by the addition of IPA to obtain a precipitate; and
f) recovering crystalline ibandronic acid Form S13.

Preferably, the halo-phosphorous compound of step a) is added slowly, in small aliquots, especially dropwise.

Form S13 can be also prepared by providing a solution of ibandronic acid in water at a temperature of about 38° C. to about 50°, cooling the solution to room temperature, followed by the addition of IPA, and maintaining the mixture at temperature for a sufficient time to obtain Form S13. Preferably, ibandronic acid is dissolved in water at a temperature of about 40° C. to provide the solution.

The following table summarizes the weight loss by TGA and water content of the novel crystalline forms of ibandronic acid described hereinabove.

| Form | Weight loss by TGA [%] | Water content by Karl Fisher [%] |
|---|---|---|
| amorphous | 5.1 | |
|  | 4.2 | |
| S1 | 3.0 | |
|  | 7.7 | 1.9 |
|  | 2.0 | 2.2 |
|  | 2.0 | |
|  | 5.2 | |
|  | 2.2 | 2.0 |
|  | 1.1 | 1.1 |
| S2 | 1.9 | |
| S3 | 17.8 | 0.5 |
| S4 | 14.8 | 0.1 |
|  | 15.2 | 0.1 |
| S5 | 13.0 | 0.7 |
|  | 14.1 | 1.1 |
|  | 2.7 | 2.3 |
|  | 1.2 | 1.1 |
| S6 | 10.1 | 2.9 |
|  | 10.9 | 1.8 |
| S7 | 13.4 | 1.2 |
|  | 11.4 | 1.9 |
| S8 | 5.5 | 0.3 |
|  | 5.6 | 0.1 |
|  | 5.3 | |
| S10 | 5.5 | 0.6 |
| S12 | 14.0 | 2.4 |
| S13 | 15.0 | 1.0 |
|  | 15.4 | |

In a further embodiment, the present invention also provides a process for purifying Ibandronic acid from inorganic impurities (i.e. reducing the amount of inorganic impurities in) that includes the step of dissolving ibandronic acid in water or methanol, and crystallizing by addition of a $C_{2-4}$ alcohol. Preferably, the $C_{2-4}$ alcohol is selected from the group consisting of ethanol, 1-propanol, IPA and tert-butanol.

In yet another embodiment, the present invention further provides a HPLC method of assaying ibandronic acid comprising the steps of: dissolving an ibandronic acid sample in a diluent to obtain a sample solution, loading the sample solution (ca. 50 μL) onto a 250×4.1 mm, Hamilton type PRP-X100 anion exchange column, eluting the sample from the column at 2.0 ml/min using a mixture of nitric acid ($HNO_3$: 35 vol-%), potassium nitrate ($KNO_3$: 45 vol-%) and ethanol (20 vol-%) as eluent, and measuring the ibandronic acid content of the relevant sample at 240 nm wavelength with a UV detector. Preferably, the diluent is water.

Some processes of the present invention involve crystallization out of a particular solvent. One skilled in the art knows that the conditions concerning crystallization can be modified without affecting the form of the polymorph obtained. For example, when mixing ibandronic acid in a solvent to form a solution, warming of the mixture may be necessary to completely dissolve the starting material. If warming does not clarify the mixture, the mixture may be diluted or filtered. To filter, the hot mixture may be passed through paper, glass fiber or other membrane material, or a clarifying agent such as celite. Depending upon the equipment used and the concentration and temperature of the solution, the filtration apparatus may need to be preheated to avoid premature crystallization. The conditions may also be changed to induce precipitation. A preferred way of inducing precipitation is to reduce the solubility of the solvent (reduce it "solubilizing power"). The solubility of the solvent—that is its ability to dissolve ibandronic acid—can be reduced, for example, by reducing the temperature of the solvent.

In yet another embodiment, the present invention provides a process for preparing ibandronate sodium (the sodium salt of ibandronic acid) comprising converting any of the solid or crystalline forms of ibandronic acid hereinabove described to ibandronate sodium by combining the ibandronic acid with an aqueous solution of sodium hydroxide at ambient temperature (about 20° to about 28° C.), concentrating the solution, especially at reduced pressure, to obtain a residue; combining the residue with acetone whereby a precipitate is formed, and recovering ibandronate monosodium.

In yet another embodiment, the present invention provides ibandronic acid having an assay of ≧99%.

In a further embodiment, the present invention provides pharmaceutical formulations that include at least on pharmaceutically acceptable excipient and one or more of the novel crystalline forms of the present invention Pharmaceutical formulations of the present invention contain solid ibandronic acid or crystalline forms thereof, such as one of those disclosed herein, optionally in a mixture with amorphous ibandronic acid. In addition to the active ingredient(s), the pharmaceutical formulations of the present invention can and typically do contain one or more pharmaceutically acceptable excipients. Such excipients are included in the formulations for a variety of purposes.

Diluents increase the bulk of a solid pharmaceutical composition, and may make a pharmaceutical dosage form containing the composition easier for the patient and care giver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol and tartaric acid.

Solid and liquid compositions (suspensions or emulsions) may also be dyed using any pharmaceutically acceptable colorant to improve their appearance and/or facilitate patient identification of the product and unit dosage level.

In liquid pharmaceutical compositions of the present invention, ibandronic acid and any other solid excipients are suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Preservatives and chelating agents such as alcohol, sodium benzoate, butylated hydroxyl toluene, butylated hydroxyanisole and ethylenediamine tetraacetic acid may be added at levels safe for ingestion to improve storage stability.

According to the present invention, a liquid composition may also contain a buffer such as guconic acid, lactic acid, citric acid or acetic acid, sodium guconate, sodium lactate, sodium citrate or sodium acetate. Selection of excipients and the amounts used may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and losenges, as well as liquid syrups, suspensions and elixirs.

The dosage form of the present invention may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

The active ingredient and excipients may be formulated into compositions and dosage forms according to methods known in the art.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

EXAMPLES

Instrumentation

X-ray diffraction data were obtained with a scintag X-Ray powder diffractometer model X'TRA, Cu-tube, solid state detector, a round standard aluminum sample holder with round zero background quartz plate was used. Scanning parameters: Range: 2-40deg.2θ: continues scan, Rate: 5 deg./min.

DSC data were obtained with a DSC821e, Mettler Toledo instrument. The sample weight was 3-5 mg. The heating (scan) rate was 10° C./min. Number of holes in the crucible: 3.

TGA data were obtained using a Mettler TG50, sample weight: 7-15 mg, heating rate: 10° C./min.

Karl Fischer data were obtained using a Mettler Toledo DL38, sample weight: 100-200 mg.

Spray drying technique were obtained using "Buchi Mini Spray dryer B-290". The spray parameters are: evaporating capacity—1 lit/hr water ( higher for organic solvents); the maximum temperature input—220° C.; Air flow—max of 35m2/hr; spray gas-compressed air or nitrogen 200-800 lit/hr, 5-8 bar; Nozzel diameter—0.7 mm (standard); Nozzel cap—1.4 mm and 1.5 mm.

Example 1

Amorphous Ibandronic Acid

An aqueous solution (40% w/w) of Ibandronic acid (150 mL) was evaporated under vacuum (20-30 mmHg) until dryness while heating the flask in a water bath (up to 70° C.) to obtain Amorphous Ibandronic acid (67 gr).

Example 2

Amorphous Ibandronic Acid

An aqueous solution (40% w/w) of Ibandronic acid (303 gr) was freeze-dried (−50° C., 0.5mmHg) for 3 days to obtain Amorphous Ibandronic acid (120 gr).

Example 3

Amorphous Ibandronic Acid

Phosphorous trichloride (3.3 mL) was added to a stirred suspension of MPPA.HCl (8 g) in silicon oil (40 mL) at 75° C. Two additional portions of phosphorous trichloride (2×3.3 mL) were added during 2 hours after heating the reaction mixture to 81° C. Two portions of phosphorus acid (2×3.1 g) were thereafter added during 2 hours. The reaction mixture was stirred at 81° C. for 22 hours. Water (40 mL) was added drop-wise at 81° C. The resulting phases were separated and the aqueous phase was heated to 90° C. for 16 hours. The obtained solution was cooled to room temperature and then was evaporated to obtain an oily residue. The oily residue was dissolved in water (7 mL) at room temperature. To the obtained solution, IPA (280 mL) was added. The obtained sticky precipitate was heated to reflux and then was cooled to room temperature, after complete dissolution. Then the IPA was decanted-off and the residue was dried in vacuum oven at 50° C. for 20 hours to obtain 4.4 g of amorphous ibandronic acid.

Example 4

Amorphous Ibandronic Acid

Phosphorous trichloride (3.3 mL) was added to a stirred suspension of MPA.HCl (8 g) in silicon oil (40 mL) at 75° C. Two additional portions of phosphorous trichloride (2×3.3 mL) were added during 2 hours after heating the reaction mixture to 81° C. Then two portions of phosphorus acid (2×3.1 g) were added during 2 hours. The reaction mixture was stirred at 81° C. for 22 hours. Water (40 mL) was added drop-wise at 81° C. Then the phases were separated and aqueous phase was heated to 90° C. for 16 hours. The obtained solution was cooled to room temperature and then was evaporated to obtain an oily residue. The oily residue was dissolved in water (7 mL) at room temperature. The obtained solution was heated to 70° C. Then hot IPA (280 mL) (73° C.) was added drop-wise. The solution was cooled to room temperature. The solution was stirred at room temperature for 21 hours. Then the IPA was decanted-off and the residue was dried in vacuum oven at 50° C. for 21 hours to obtain 4.6 g of amorphous ibandronic acid.

Example 5

Ibandronic Acid Crystal Form S1

Amorphous ibandronic acid (3.0 g) was dissolved in water (4 mL) at room temperature. Acetone (70 mL) was added to the stirred solution. White slurry was obtained while stirring at room temperature for 68 hours. The precipitate was isolated by vacuum filtration, washed with acetone (2×25 mL) and dried in a vacuum oven at 50° C. for 24hours to obtain 2.5 g of ibandronic acid crystal form S1.

Example 6

Ibandronic Acid Crystal Form S1

40% w/w aqueous solution of ibandronic acid (22.2 g) was concentrated under vacuum. To the concentrated solution (15.71 g), tert-butanol was added drop-wise at room temperature in two portions (2×50 mL) and the mixture was stirred at this temperature for 4 hours. The obtained precipitate was isolated by vacuum filtration, washed with tert-butanol (1×15 mL) and dried in a vacuum oven at 5° C. for 24 hours to obtain 5.5 g of ibandronic acid crystal form S1.

Example 7

Ibandronic Acid Crystal Form S1

40% w/w aqueous solution of ibandronic acid (16.8 g) was concentrated under vacuum. To the concentrated solution (12.1 g), absolute Ethanol (100 mL) was added drop-wise at room temperature and the mixture was stirred at this temperature for 4.5 hours. The obtained precipitate was isolated by vacuum filtration, washed with absolute Ethanol (2×25 mL) and dried in a vacuum oven at 50° C. for 23 hours to obtain 5.2 g of ibandronic acid crystal form S1.

Example 8

Ibandronic Acid Crystal Form S1

Amorphous ibandronic acid (3.0 g) was dissolved in methanol (12 mL) at room temperature. Acetone (40 mL) was added in one portion to the stirred solution. The obtained slurry was stirred at room temperature for 72 hours. The resulting precipitate was isolated by vacuum filtration, washed with acetone (2×12.5 mL) and dried in a vacuum oven at 50° C. for 22 hours to obtain 2.5 g of ibandronic acid crystal form S1.

Example 9

Ibandronic Acid Crystal Form S1

Amorphous ibandronic acid (3.0 g) was stirred in acetone (15 mL) at reflux temperature for 5 hours. The slurry was cooled to room temperature and then it was stirred at this temperature for 16 hours. The product was dried in a vacuum oven at 50° C. for 24 hours to obtain 2.8 g of ibandronic acid crystal form S1.

Example 10

Ibandronic Acid Crystal Form S1

Amorphous ibandronic acid (3.0 g) was stirred in absolute ethanol (20 mL) at reflux temperature for 2.5 hours. The slurry was cooled to room temperature and then it was stirred at this temperature for 40.5 hours. The product was isolated by vacuum filtration, washed with absolute ethanol (2×20 mL) and dried in a vacuum oven at 40° C. for 25 hours to obtain 2.8 g of ibandronic acid crystal form S1.

Example 11

Ibandronic Acid Crystal Form S1

40% w/w aqueous solution of ibandronic acid (10.95 g) was concentrated under vacuum. To the concentrated solution (7.5 g), acetone was added at room temperature in two portions (2×45 mL) and the mixture was stirred at this temperature for 22 hours. The obtained precipitate was isolated by vacuum filtration, washed with Acetone (2×20 mL) and dried in a vacuum oven at 50° C. for 70 hours to obtain 2.9 g of ibandronic acid crystal form S1.

Example 12

Ibandronic Acid Crystal Form S1

Phosphorous oxychloride (17 mL) was added drop-wise to a stirred suspension of MPA.HCl (10 g) and phosphorous acid (14.8 g) in toluene (70 mL) at 75° C. The reaction mixture was heated to 80° C. and was stirred at this temperature for 26 hours. The reaction mixture was cooled to room temperature. The toluene was decanted-off and the residue was stirred under reflux with water (70 mL) for 15.5 hours. The obtained solution was cooled to room temperature and then was evaporated to obtain an oily residue (34.3 g). Absolute ethanol (853 mL) was added gradually to the oily reside while stirring at room temperature during 45 hours. The obtained precipitate was isolated by vacuum filtration, washed with absolute ethanol (2×97 mL) and dried in a vacuum oven at 50° C. for 24 hours to obtain 6.7 g of ibandronic acid crystal form S1.

Example 13

Ibandronic Acid Crystal Form S2

Amorphous ibandronic acid (3.0 g) was dissolved in methanol (12 mL) at room temperature. Acetonitrile (ACN) (40 mL) was added in one portion to the stirred solution. The obtained slurry was stirred at room temperature for 72 hours. The precipitate was isolated by vacuum filtration, washed with ACN (2×20 mL) and dried in a vacuum oven at 50° C. for 21.5 hours to obtain 2.4 g of ibandronic acid crystal form S2.

Example 14

Ibandronic Acid Crystal Form S3

40% w/w aqueous solution of ibandronic acid (11 g) was concentrated under vacuum. To the concentrated solution (7.6 g), tert-butanol (50 mL) was added at room temperature. The obtained slurry was stirred at this temperature for 72 hours. Then the precipitate was isolated by vacuum filtration, washed with tert-butanol (2×40 mL) and dried in a vacuum oven at 50° C. for 22.5 hours to obtain 4.2 g of ibandronic acid crystal form S3.

Example 15

Ibandronic Acid Crystal Form S4

40% w/w aqueous solution of ibandronic acid (19.7 g) was concentrated under vacuum. To the concentrated solution (12.5 g), 1-propanol (150 mL) was added gradually at room temperature. The un-stirrable product was heated to reflux to obtain viscous stirrable mixture. The mixture was cooled to room temperature and stirred at this temperature for 16 hours. The obtained precipitate was isolated by vacuum filtration, washed with 1-propanol (2×17 mL) and dried in a vacuum oven at 50° C. for 24 hours to obtain 6.6 g of ibandronic acid crystal form S4.

Example 16

40% w/w aqueous solution of ibandronic acid (23.7 g) was concentrated under vacuum. To the concentrated solution (14 g), 1-propanol (100 mL) was added drop-wise at room temperature and the mixture was stirred at this temperature for 3 hours. The obtained precipitate was isolated by vacuum filtration, washed with 1-propanol (2×35 mL) and dried in a vacuum oven at 50° C. for 24 hours to obtain 10.2 g of ibandronic acid crystal form S4.

Example 17

Ibandronic Acid Crystal Form S5

Phosphorous trichloride (10.9 mL) was added drop-wise to a stirred suspension of MPA.HCl (7 g) and phosphorous acid (10.3 g) in silicon oil (49 mL) at 75° C. The reaction mixture was heated to 80° C. Two additional portions of phosphorous trichloride (1×1.5 ml and 1×1 mL) were added gradually to the stirred reaction mixture at ~80° C. The reaction mixture was stirred at this temperature for 50 hours. Water (49 mL) was added drop-wise at 79° C. The phases were separated and the aqueous phase was heated to reflux for 15.5hours. The obtained solution was cooled to room temperature and then was evaporated until dryness to obtain an oily residue (27.2 g). The oily residue was dissolved in water (4 mL). To the obtained solution, IPA (209 mL) was added drop-wise at room temperature and the mixture was stirred at this temperature for 24 hours. The obtained precipitate was isolated by vacuum filtration, washed with IPA (2×52 mL) and dried in a vacuum oven at 50° C. for 24 hours to obtain 9.9 g of ibandronic acid crystal form S5.

Example 18

Ibandronic Acid Crystal Form S5

Phosphorous trichloride (8.2 mL) was added drop-wise to a stirred suspension of MPA.HCl (7 g) and phosphorous acid (3.9 g) in toluene (35 mL) at 75° C. The reaction mixture was heated to 95° C. and was stirred at this temperature for 23 hours. The toluene was decanted-off and the residue was stirred under reflux (96° C.) with 6N HCl (104 mL) for 43 hours. The obtained solution was cooled to room temperature and was then concentrated to obtain an oily residue (8.1 g). The oily residue was dissolved in water (4 mL). To the obtained solution, IPA (196 mL) was added drop-wise at room temperature and the mixture was stirred at this temperature for 72 hours. The obtained precipitate was isolated by vacuum filtration, washed with IPA (2×40 mL) and dried in a vacuum oven at 50° C. for 24 hours to obtain 4.5 g of ibandronic acid crystal form S5.

Example 19

Ibandronic Acid Crystal Form S5

Phosphorous oxychloride (50 mL) was added drop-wise to a stirred suspension of MPA.HCl (30 g) and phosphorous acid (44 g) in silicone oil (210 mL) at 75° C. The reaction mixture was heated to 81° C. Two additional portions of phosphorous oxychloride (1×6.7 ml and 1×4 mL) were added gradually to the stirred reaction mixture at 81° C. The reaction mixture was stirred at this temperature for 50 hours. Water (210 mL) was added drop-wise to the solution and the mixture was stirred for 1 hr. Then the phases were separated and the aqueous phase was heated to reflux for 16.5 hours. The obtained solution was cooled to room temperature and then was evaporated until dryness to obtain an oily residue (125.6 g). The oily residue was dissolved in water (19 mL). To the obtained solution, IPA (1760 mL) was added at room temperature and the mixture was stirred at this temperature for 24 hours and then was cooled to 7° C. and stirred this temperature for 72 hrs. The obtained precipitate was isolated by vacuum filtration, washed with IPA (2×100 mL) and dried in a vacuum oven at 50° C. for 25 hours to obtain 22 g of ibandronic acid crystal form S5.

Example 20

Ibandronic Acid Crystal Form S5

Amorphous ibandronic acid (3.0 g) was stirred in THF (20 mL) at reflux temperature for 2.5 hours to obtain almost complete dissolution. The mixture was cooled to room temperature and then it was stirred at this temperature for 21 hours. The obtained precipitate was isolated by vacuum filtration under nitrogen flow, washed with THF (2×15 mL) and dried in a vacuum oven at 40° C. for 23.5 hours to obtain 2.7 g of ibandronic acid crystal form S5.

Example 21

Ibandronic Acid Crystal Form S5

Amorphous ibandronic acid (3.0 g) was stirred in Absolute Ethanol (30 mL) at room temperature. The slurry was stirred at room temperature for 72 hours. The product was isolated by vacuum filtration, washed with Absolute Ethanol (2×20 mL) and dried in a vacuum oven at 50° C. for 22 hours to obtain 2.9 g of ibandronic acid crystal form S5.

Example 22

Ibandronic Acid Crystal Form S5

Phosphorous oxychloride (17 mL) was added drop-wise to a stirred suspension of MPA.HCl (10 g) and phosphorous acid (14.8 g) in toluene (70 mL) at 75° C. The reaction mixture was heated to 80° C. and was stirred at this temperature for 26 hours. The reaction mixture was cooled to room temperature. The toluene was decanted-off and the residue was stirred under reflux with water (70 mL) for 15.5 hours. The obtained solution was cooled to room temperature and then was evaporated until dryness to obtain an oily residue (34.3 g). IPA (834 mL) was added gradually to the oily reside while stirring at room temperature during 72 hours. The obtained precipitate was isolated by vacuum filtration, washed with IPA (2×84 mL) and dried in a vacuum oven at 50° C. for 23 hours to obtain 12.8 g of ibandronic acid crystal form S5.

Example 23

Ibandronic Acid Crystal Form S5

Phosphorous trichloride (15.6 mL) was added drop-wise to a stirred suspension of MPA.HCl (10 g) and phosphorous acid (14.7 g) in silicon oil (70 mL) at 75° C. The reaction mixture was heated to 80° C. Two additional portions of phosphorous trichloride (1×2 ml and 1×1.3 mL) were added gradually to the stirred reaction mixture at 80° C. The reaction mixture was stirred at this temperature for 48 hours. Water (70 mL) was added drop-wise at 80° C. The phases were separated and the aqueous phase was heated to reflux for 16hours. The obtained solution was cooled to room temperature and then was evaporated until dryness to obtain an oily residue (38.2 g). IPA (746 mL) was added to the oily residue at room temperature and the mixture was stirred at this temperature for 53.5 hours. The obtained precipitate was isolated by vacuum filtration, washed with IPA (2×83 mL) and dried in a vacuum oven at 50° C. for 24.5 hours to obtain 11.1 g of ibandronic acid crystal form S5.

Example 24

Ibandronic Acid Crystal Form S6

Phosphorous trichloride (10.9 mL) was added drop-wise to a stirred suspension of MPPA.HCl (7 g) and phosphorous acid (10.3 g) in silicon oil (49 mL) at 75° C. The reaction mixture was heated to 80° C. Two additional portions of phosphorous trichloride (1×1.5 ml and 1×1 mL) were added gradually to the stirred reaction mixture at ~80° C. The reaction mixture was stirred at this temperature for 50 hours. Water (49 mL) was added drop-wise at 79° C. The phases were separated and the aqueous phase was heated to reflux for 15.5hours. The obtained solution was cooled to room temperature and then was evaporated until dryness to obtain an oily residue (27.2 g). The oily residue was dissolved in water (3.8 mL). To the obtained solution, tert-butanol (191 mL) was added at room temperature and the mixture was stirred at this temperature for 42 hours. The obtained precipitate was isolated by vacuum filtration, washed with tert-butanol (2×38 mL) and dried in a vacuum oven at 50° C. for 25.5 hours to obtain 6.2 g of ibandronic acid crystal form S6.

Example 25

Phosphorous trichloride (8.2 mL) was added drop-wise to a stirred suspension of MPA.HCl (7 g) and phosphorous acid (3.9 g) in toluene (35 mL) at 75° C. The reaction mixture was heated to 95° C. and was stirred at this temperature for 23 hours. The Toluene was decanted-off and the residue was stirred under reflux (96° C.) with 6H HCl (104 mL) for 43 hours. The obtained solution was cooled to room temperature and then was evaporated until dryness to obtain an oily residue (8.1 g). The oily residue was dissolved in water (4 mL). To the obtained solution, tert-butanol (204 mL) was added drop-wise at room temperature and the mixture was stirred at this temperature for 72 hours. The obtained precipitate was isolated by vacuum filtration, washed with tert-butanol (2×40 mL) and dried in a vacuum oven at 50° C. for 23 hours to obtain 2.8 g of ibandronic acid crystal form S6.

Example 26

Ibandronic Acid Crystal Form S7

Phosphorous trichloride (15.6 mL) was added drop-wise to a stirred suspension of MPA.HCl (10 g) and phosphorous acid (14.7 g) in silicon oil (70 mL) at 70° C. The reaction mixture was heated to 80° C. and was stirred at this temperature for 23.5 hours. Water (70 mL) was added drop-wise at 80° C. Then the phases were separated and the aqueous phase was heated to reflux for 18 hours. The obtained solution was cooled to room temperature and then was evaporated until dryness to obtain an oily residue (24.5 g). IPA (443 mL) was added gradually to the oily residue and the mixture was stirred at room temperature for 18 hours. The obtained precipitate was isolated by vacuum filtration, washed with IPA (1×80 mL) and dried in a vacuum oven at 50° C. for 24 hours to obtain 9.8 g of ibandronic acid crystal form S7.

Example 27

Ibandronic Acid Crystal Form S7

Phosphorous oxychloride (17 mL) was added drop-wise to a stirred suspension of MPA.HCl (10 g) and phosphorous acid (14.8 g) in toluene (70 mL) at 75° C. The reaction mixture was heated to 80° C. and was stirred at this temperature for 26 hours. Then the reaction mixture was cooled to room temperature. The toluene was decanted-off and the residue was stirred under reflux with water (70 mL) for 15.5 hours. The obtained solution was cooled to room temperature and then was evaporated until dryness to obtain an oily residue (34.3 g). 1-Propanol (695 mL) was added gradually to the oily reside while stirring at room temperature during 18 hours. The obtained precipitate was isolated by vacuum filtration, washed with 1-propanol (2×39 mL) and dried in a vacuum oven at 50° C. for 24hours to obtain 10.8 g of ibandronic acid crystal form S7.

Example 28

Ibandronic Acid Crystal Form S8

Phosphorous trichloride (18.7 mL) was added drop-wise to a stirred suspension of MPA.HCl (12 g) and phosphorous acid (17.6 g) in silicone oil (84 mL) at 75° C. The reaction mixture was heated to 80° C. Two additional portions of phosphorous trichloride (1×2.5 ml and 1×1.5 mL) were added gradually to the stirred reaction mixture at 80° C. The reaction mixture was stirred at this temperature for 51.5 hours. Water (84 mL) was added drop-wise to the solution, stirred for 15 minutes. The phases were separated and the aqueous phase was heated to reflux for 16 hours. The obtained solution was cooled to room temperature and stirred at this temperature for 12 hours. A portion (23 mL) of this solution (24.8 g) was concentrated to obtain an oily residue (11.26 g). The oily residue was dissolved in water (1.7 mL). To the obtained solution, IPA (87 mL) was added drop-wise at room temperature and the mixture was stirred at this temperature for 70 hours. The obtained precipitate was isolated by vacuum filtration, washed with IPA (2×25 mL) and dried in a vacuum oven at 50° C. for 25 hours to obtain 3.27 g of ibandronic acid crystal form S8.

Example 29

Ibandronic Acid Crystal Form S8

Phosphorous trichloride (18.7 mL) was added drop-wise to a stirred suspension of MPA.HCl (12 g) and phosphorous acid (17.6 g) in silicone oil (84 mL) at 75° C. The reaction mixture was heated to 80° C. Two additional portions of phosphorous trichloride (1×2.5 ml and 1×1.5 mL) were added gradually to the stirred reaction mixture at 80° C. The reaction mixture was stirred at this temperature for 51.5 hours. Water (84 mL) was added drop-wise to the solution and the mixture stirred for 15 minutes. The phases were separated and the aqueous phase was heated to reflux for 16 hours. The obtained solution was cooled to room temperature and stirred at this temperature for 12 hours. A portion (23 mL) from this solution (27 g) was evaporated until dryness to obtain an oily residue (11 g). The oily residue was dissolved in water (1.6 mL). To the obtained solution, 1-propanol (160 mL) was added drop-wise at room temperature and the mixture was stirred at this temperature for 20 hours. The obtained precipitate was isolated by vacuum filtration, washed with IPA (2×10 mL) and dried in a vacuum oven at 50° C. for 25 hours to obtain 3.16 g of ibandronic acid crystal form S8.

Example 30

Ibandronic Acid Crystal Form S8

Phosphorous oxychloride (20 mL) was added drop-wise to a stirred suspension of MPA.HCl (12 g) and phosphorous acid (17.6 g) in Silicone oil (84 mL) at 75° C. The reaction mixture was heated to 80° C. Two additional portions of phosphorous oxychloride (1×2.7 ml and 1×1.6 mL) were added gradually to the stirred reaction mixture at 80° C. The reaction mixture was stirred at this temperature for 50 hours. Water (84 mL) was added drop-wise to the solution, stirred for 20 minutes. The phases were separated and the aqueous phase was heated to reflux for 17 hours. The obtained solution was cooled to room temperature and stirred at this temperature for 12 hours. A portion (24 mL) from this solution (24 g) was concentrated to obtain an oily residue (21.65 g). The oily residue was dissolved in water (1.9 mL). To the obtained solution, IPA (177 mL) was added drop-wise at room temperature and the mixture was stirred at this temperature for 23 hours. The obtained precipitate was isolated by vacuum filtration, washed with IPA (2×20 mL) and dried in a vacuum oven at 50° C. for 26.5 hours to obtain 2.37 g of ibandronic acid crystal form S8.

Example 31

Ibandronic Acid Crystal Form S8

Phosphorous trichloride (15.6 mL) was added drop-wise to a stirred suspension of MPA.HCl (10 g) and phosphorous acid (14.7 g) in silicon oil (70 mL) at 75° C. The reaction mixture was heated to 80° C. Two additional portions of phosphorous trichloride (1×2 ml and 1×1.3 mL) were added gradually to the stirred reaction mixture at 80° C. The reaction mixture was stirred at this temperature for 48 hours. Water (70 mL) was added drop-wise at 80° C. Then the phases were separated and the aqueous phase was heated to reflux for 16 hours. The obtained solution was cooled to room temperature and then was evaporated until dryness to obtain an oily residue (38.2 g). Absolute ethanol (766 mL) was added to the oily residue at room temperature and the mixture was stirred at this temperature for 53 hours. The obtained precipitate was isolated by vacuum filtration, washed with absolute ethanol (2×61 mL) and dried in a vacuum oven at 50° C. for 25.5 hours to obtain 7.7 g of ibandronic acid crystal form S8.

Example 32

Ibandronic Acid Crystal Form S8

Phosphorous trichloride (57 mL) was added drop-wise to a stirred suspension of MPA.HCl (30 g) and phosphorous acid (44 g) in silicon oil (210 mL) at 75° C. The reaction mixture was heated to 80° C. Two additional portions of phosphorous trichloride (1×6.25 ml and 1×3.75 mL) were added gradually to the stirred reaction mixture at 80° C. The reaction mixture was stirred at this temperature for 48 hours. Water (210 mL) was added drop-wise at 80° C. and stirred at this temperature for 30 minutes. Then the phases were separated and the aqueous phase was heated to reflux for 17 hours. The solution was cooled to room temperature and then concentrated to obtain an oily residue (121.1 g). The oily residue was dissolved in water (18 mL). Absolute ethanol (3027 mL) was added to the solution at room temperature and the mixture was stirred at this temperature for 72 hours. Cooling to 5° C. and stirring at this temperature for 7 hours. The obtained precipitate was isolated by vacuum filtration, washed with absolute ethanol (2×48 mL) and dried in a vacuum oven at 50° C. for 23.5 hours to obtain 35.64 g of ibandronic acid crystal form S8.

Example 33

Ibandronic Acid Crystal Form S10

Phosphorous oxychloride (50 mL) was added drop-wise to a stirred suspension of MPA.HCl (30 g) and phosphorous acid (44 g) in silicon oil (210 mL) at 75° C. The reaction mixture was heated to 80° C. Two additional portions of phosphorous oxychloride (1×6.7 ml and 1×4 mL) were added gradually to the stirred reaction mixture at 80° C. The reaction mixture was stirred at this temperature for 51 hours. Water (210 mL) was added drop-wise at 80° C. and stirred at this temperature for 30 minutes. Then the phases were separated and the aqueous phase was heated to reflux for 16.5 hours. The solution was cooled to room temperature and then was evaporated until dryness to obtain an oily residue (128.5 g). The oily residue was dissolved in water (19 mL). Absolute ethanol (3210 mL) was added to the solution at room temperature and the mixture was stirred at this temperature for 39 hours. The mixture was seeded with ibandronic acid and stirred for 4.5 hours. The mixture was cooled to 0° C. and stirred at this temperature for 72 hours. The obtained precipitate was isolated by vacuum filtration, washed with absolute ethanol and dried in a vacuum oven at 50° C. for 23 hours to obtain 13.82 g of ibandronic acid crystal form S10.

Example 34

Ibandronic Acid Crystal Form S10

Phosphorous trichloride (15.6 mL) was added drop-wise to a stirred suspension of MPA.HCl (10 g) and phosphorous acid (14.7 g) in silicon oil (70 mL) at 70° C. The reaction mixture was heated to 80° C. and was stirred at this temperature for 23.5 hours. Water (70 mL) was added drop-wise at 80° C. The phases were separated and the aqueous phase was heated to reflux for 18 hours. The obtained solution was cooled to room temperature and then concentrated to obtain an oily residue (24.5 g). Absolute ethanol (597 mL) was added to the oily residue and the mixture was stirred at room temperature for 20.5 hours. The obtained precipitate was isolated by vacuum filtration, washed with absolute ethanol (2×20 mL) and dried in a vacuum oven at 50° C. for 31 hours to obtain 7.3 g of ibandronic acid crystal form S10.

Example 35

Ibandronic Acid Crystal Form S10

Phosphorous trichloride (18.7 mL) was added drop-wise to a stirred suspension of MPA.HCl (12 g) and phosphorous acid (17.6 g) in silicone oil (84 mL) at 75° C. The reaction mixture was heated to 80° C. Two additional portions of phosphorous trichloride (1×2.5 ml and 1×1.5 mL) were added gradually to the stirred reaction mixture at 80° C. The reaction mixture was stirred at this temperature for 52 hours. Water (84 mL) was added drop-wise to the solution, stirred for 15 minutes. Then the phases were separated and the aqueous phase was heated to reflux for 16 hours. The obtained solution was cooled to room temperature and stirred at this temperature for 13 hours. A portion (23 mL) from this solution (27.31 g) was evaporated until dryness to obtain an oily residue (11.25 g). The oily residue was dissolved in water (1.7 mL). To the obtained solution, abs. ethanol (270 mL) was added drop-wise at room temperature and the mixture was stirred at this temperature for 20 hours. The obtained precipitate was isolated by vacuum filtration, washed with abs ethanol (2×12.5 mL) and dried in a vacuum oven at 50° C. for 24 hours to obtain 8.56 g of ibandronic acid crystal form S10.

Example 36

Ibandronic Acid Crystal Form S10

Phosphorous oxychloride (20 mL) was added drop-wise to a stirred suspension of MPA.HCl (12 g) and phosphorous acid (17.6 g) in silicone oil (84 mL) at 75° C. The reaction mixture was heated to 80° C. Two additional portions of phosphorous oxychloride (1×2.7 ml and 1×1.6 mL) were added gradually to the stirred reaction mixture at 80° C. The reaction mixture was stirred at this temperature for 50 hours. Water (84 mL) was added drop-wise to the solution, stirred for 20 minutes. The phases were separated and the aqueous phase was heated to reflux for 13 hours. The obtained solution was cooled to room temperature and stirred at this temperature for 12 hours. A portion (24 mL) from this solution (29 g) was concentrated to obtain an oily residue (12.8 g). The oily residue was dissolved in water (1.9 mL). To the obtained solution, abs. ethanol (300 mL) was added drop-wise at room temperature and the mixture was stirred at this temperature for 25 hours. The obtained precipitate was isolated by vacuum filtration, washed with abs. ethanol (2×20 mL) and dried in a vacuum oven at 50° C. for 24 hours to obtain 1.81 g of ibandronic acid crystal form S10.

Example 37

Ibandronic Acid Crystal Form S12

Phosphorous trichloride (15.6 mL) was added drop-wise to a stirred suspension of MPA.HCl (10 g) and phosphorous acid (14.7 g) in silicon oil (70 mL) at 70° C. The reaction mixture was heated to 80° C. and was stirred at this temperature for 23.5 hours. Water (70 mL) was added drop-wise at 80° C. The phases were separated and the aqueous phase was heated to reflux for 18 hours. The obtained solution was cooled to room temperature and then was evaporated until dryness to obtain an oily residue (24.5 g). 1-Propanol was added to the oily residue at room temperature in two portions (2×25 mL) and the mixture was stirred at this temperature for 17.5 hours. The obtained precipitate was isolated by vacuum filtration, washed with 1-propanol (2×20 mL) and dried in a vacuum oven at 50° C. for 22.5 hours to obtain 10.1 g of ibandronic acid crystal form S12.

Example 38

Ibandronic Acid Crystal Form S13

Phosphorous oxychloride (11.7 mL) was added drop-wise to a stirred suspension of MPA.HCl (7 g) and phosphorous acid (10.3 g) in silicon oil (49 mL) at 75° C. The reaction mixture was heated to 80° C. An additional portion of phosphorous oxychloride (1×1.6 mL) was added to the reaction mixture at 80° C. after 45.5 hours. The reaction mixture was stirred at 80° C. for additional 2.5 hours. Water (49 mL) was added drop-wise at 80° C. The phases were separated and the aqueous phase was heated to 100° C. for 18 hours. The obtained solution was cooled to room temperature and then was concentrated to obtain an oily residue (26.7 g). The oily residue was dissolved in water (4 mL). To the obtained solution, IPA (360 mL) was added drop-wise while stirring at room temperature during 48 hours. The obtained precipitate was isolated by vacuum filtration, washed with EPA (1×20 mL) and dried in a vacuum oven at 50° C. for 24.5 hours to obtain 1.84 g of ibandronic acid crystal form S13.

Example 39

Ibandronic Acid Crystal Form S13

MPA.HCl (7 g) was added to melted phosphorous acid (3.4 g) while stirring in an oil-bath at 95° C. Phosphorous trichloride (5.8 mL) was added drop-wise. The mixture was stirred at 95-100° C. (in an oil-bath) for 25.5 hours. Without cooling, but removing the oil-bath, water (21 mL) was added drop-wise. The reaction mixture was stirred at 97° C. for 16 hours. The obtained solution was cooled to room temperature. Insoluble particles were filtered off and the filtrate was concentrated to obtain an oily residue (12.9 g). The oily residue was dissolved in water (1.9 mL). To the obtained solution, IPA (290 mL) was added gradually while stirring at room temperature during 100 hours. The obtained precipitate was isolated by vacuum filtration, washed with IPA (2×30 mL) and dried in a vacuum oven at 50° C. for 24 hours to obtain 8.11 g of ibandronic acid crystal form S13.

Example 40

Ibandronic Acid Crystal Form S13

Phosphorous trichloride (50 mL) was added drop-wise to a stirred suspension of MPA.HCl (30 g) and phosphorous acid (44 g) in silicone oil (210 mL) at 75° C. The reaction mixture was heated to 80° C. Two additional portions of phosphorous trichloride (1×6.25 ml and 1×3.75 mL) were added gradually to the stirred reaction mixture at 80° C. The reaction mixture was stirred at this temperature for 48.5 hours. Water (210 mL) was added drop-wise to the solution and the mixture stirred for 15 minutes. The phases were separated and the aqueous phase was heated to reflux for 16.5 hours. The obtained solution was cooled to room temperature and then was concentrated to obtain an oily residue (121.3 g). The oily residue was dissolved in water (18 mL). To the obtained solution, IPA (1698 mL) was added at room temperature and the mixture was stirred at this temperature for 22 hours and then was cooled to 4° C. and stirred this temperature for 4 hrs. The obtained precipitate was isolated by vacuum filtration, washed with IPA (2×43 mL) and dried in a vacuum oven at 50° C. for 47 hours to obtain 39 g of ibandronic acid crystal form S13.

Example 41

Ibandronic Acid Crystal Form S13

Ibandronic acid (97 g) was dissolved in water (90 mL) at 40° C. The solution was cooled to room temperature and IPA (1100 mL) was added, stirred at this temperature for 22 hrs. The obtained precipitate was isolated by vacuum filtration, washed with IPA (2×50 mL) and dried in a vacuum oven at 50° C. for 25 hours to obtain 97.6 g of ibandronic acid crystal form S13.

Example 42

Comparative Example—Repetition of Example 9 of U.S. Pat. No. 4,927,814

15 g N-Methyl-N-pentylaminopropionic acid (MPA.HCl) were kept for 23 hours at 100° C. with 8.8 g phosphorous acid and 18.7 ml phosphorous trichloride in 75 ml chlorobenzene. The solvent was then decanted off and the residue was stirred under reflux with 222 ml 6N HCl for 12.5 hours. Insoluble material was filtered off and the filtrate was concentrated and applied to column of Amberlite IR 120 (H+). The elution with water was monitored by HPLC. The desired fractions were combined, evaporated and stirred up with acetone to obtain a sticky oily precipitate as a crude product. (The HPLC method for monitoring the ion-exchange chromatography is the one described in this application).

Example 43

Comparative Example—Repetition of Example 9 of U.S. Pat. No. 4,927,814—with Methyl Ethyl Ketone used Instead of Acetone 15 g N-Methyl-N-pentylaminopropionic acid (MPA.HCl) were kept for 23 hours at 100° C. with 8.8 g phosphorous acid and 18.7 ml phosphorous trichloride in 75 ml chlorobenzene. The solvent was then decanted off and the residue was stirred under reflux with 222 ml 6N HCl for 12.5 hours. Insoluble material was filtered off and the filtrate was concentrated and applied to column of Amberlite IR 120 (H+). The elution with water was monitored by HPLC. The desired fractions were combined, evaporated and stirred up with methyl ethyl ketone (MEK) to obtain a sticky oily precipitate as a crude product. (The HPLC method for monitoring the ion-exchange chromatography is the one described in this application).

Example 44

Comparative Example—Repetition of Example 9 of U.S. Pat. No. 4,927,814—with Acetonitrile used Instead of Acetone 15 g N-Methyl-N-pentylaminopropionic acid (MPA.HCl) were kept for 23 hours at 100° C. with 8.8 g phosphorous acid and 18.7 ml phosphorous trichloride in 75 ml chlorobenzene. The solvent was then decanted off and the residue was stirred under reflux with 222 ml 6N HCl for 12.5 hours. Insoluble material was filtered off and the filtrate was concentrated and applied to column of Amberlite IR 120 (H+). The elution with water was monitored by HPLC. The desired fractions were combined, evaporated and stirred up with acetonitrile to obtain a sticky oily precipitate as a crude product. (The HPLC method for monitoring the ion-exchange chromatography is the one described in this application).

HPLC assay
Column: Hamilton type PRP-X100, Anion exchange, 250*4.1 mm
Temp.: 35° C.
Eluent: 35% $HNO_3$, 45% $KNO_3$, 20% EtOH
Flow: 2.0 mL/min
Diluent: $H_2O$
Injection volume: 50 μL
Detector: 240 nm
The following samples were analyzed according to the above method:

| Example No. | Crystal-lization medium | Polymorph | % area of $PO_4^{-3}$ | % area of $PO_3^{-3}$ | % area of $Cl^-$ |
|---|---|---|---|---|---|
| 32 | EtOH | S8 | | 0.4 | ND* |
| 33 | EtOH | S10 | 0.2 | 0.2 | ND* |

*ND = not detected

Example 45

Amorphous Ibandronic Acid

Ibandronic acid (9 g) was dissolved in water (18 ml) at room temperature. The solution was divided into three portions, and each portion was spray dried using a Buchi mini spray dryer B-290 using a standard nozzle 0.7 mm in diameter with a nozzle cap of 1.4 or 1.5 mm. The solution feed rate was about 1 L/h. The spray gas was set at 200-800L/h at a pressure of 5-8 bar. In each instance, amorphous ibandronic acid was obtained.

For portion 1, nitrogen gas was at an inlet temperature of 50° C. The evaporated solvent and nitrogen left the spray dryer at a temperature of 41-36° C.

For portion 2, nitrogen gas was at an inlet temperature of 100° C. The evaporated solvent and nitrogen left the spray dryer at a temperature of 71-72° C.

For portion 3, nitrogen gas was at an inlet temperature of 150° C. The evaporated solvent and nitrogen left the spray dryer at a temperature of 100° C.

Each of the three product was analyzed by powder x-ray diffraction and found to be amorphous.

Example 46

Conversion of Ibandronic Acid to Monosodium Ibandronate

Ibandronic acid (4.5 g) was dissolved in water (45 ml) at room temperature. A solution of 1N aq. NaOH (14 ml) was added in one portion. The reaction mixture was stirred at room temperature for 2.5 hours . Then the solution was concentrated under reduced pressure and was poured into Acetone (45 ml) at room temperature. A white precipitate was obtained immediately. The obtained slurry was stirred at room temperature for 72 hours. The product was isolated by vacuum filtration, washed with Acetone (2×20ml) and dried in a vacuum oven at 50° C. for 22 hours to obtain 4.45 g of ibandronate monosodium salt (pH=4.26).

What is claimed is:

1. A process for preparing solid ibandronic acid comprising the steps of:
   a) combining a halo-phosphorous compound and phosphorous acid with N-methyl-N-pentyl propionic acid or a hydrochloride salt of N-methyl-N-pentyl propionic acid in a diluent selected from the group consisting of silicone oil, toluene and a mixture of toluene and phosphoric acid to form a mixture;
   b) heating the mixture to a temperature of about 80° C. to about 100° C.;
   c) combining the mixture with water to form a biphasic mixture having aqueous and organic phases;
   d) separating the aqueous and organic phases;
   e) heating the aqueous phase at a temperature of about 95° C. to about 110° C.;
   f) evaporating the aqueous phase to obtain a residue of ibandronic acid;
   g) combining the residue with a $C_{2-4}$ alcohol or acetone to obtain a mixture having a precipitate of solid ibandronic acid; and
   h) recovering the precipitated solid ibandronic acid from the mixture.

2. The process according to claim 1, wherein the combining of step a) is performed by adding the halo-phosphorous compound in small aliquots to a mixture of the phosphorous acid, the N-methyl-N-pentyl propionic acid or hydrochloride salt of N-methyl -N-pentyl propionic acid, and the diluent.

3. The process according to claim 1, wherein the combining of step a) is performed at a temperature of about 70° C. to about 78° C.

4. The process according to claim 1, wherein the mixture in step b) is heated to a temperature of about 80° C.

5. The process according to claim 1, wherein the $C_{2-4}$ alcohol is selected from the group consisting of ethanol, 1-propanol, isopropyl alcohol and tert-butanol.

6. The process according to claim 5, wherein the $C_{2-4}$ alcohol is ethanol or isopropyl alcohol.

7. The process according to claim 1, wherein the residue of step f) is combined with water prior to combining with the $C_{2-4}$ alcohol.

8. The process according to claim 1, wherein the mixture of step g) is heated in order to facilitate the formation of the precipitate of the solid ibandronic acid.

9. The process of claim 1 wherein the halo-phosphorous compound is phosphorous trichloride or phosphorous oxychloride.

* * * * *